US010634589B2

(12) United States Patent
Shultz et al.

(10) Patent No.: US 10,634,589 B2
(45) Date of Patent: Apr. 28, 2020

(54) METHODS OF REDUCING OR ELIMINATING PROTEIN MODIFICATION AND DEGRADATION ARISING FROM EXPOSURE TO UV LIGHT

(71) Applicant: Amgen Inc., Thousand Oaks, CA (US)

(72) Inventors: Joseph Edward Shultz, Binningen (CH); Roger Hart, Loveland, CA (US); Brent Welborn, Camarillo, CA (US)

(73) Assignee: AMGEN INC., Thousand Oaks, CA (US)

( * ) Notice: Subject to any disclaimer, the term of this patent is extended or adjusted under 35 U.S.C. 154(b) by 21 days.

(21) Appl. No.: 14/353,704

(22) PCT Filed: Oct. 25, 2012

(86) PCT No.: PCT/US2012/061965
§ 371 (c)(1),
(2) Date: Apr. 23, 2014

(87) PCT Pub. No.: WO2013/063298
PCT Pub. Date: May 2, 2013

(65) Prior Publication Data

US 2014/0329227 A1 Nov. 6, 2014

Related U.S. Application Data

(60) Provisional application No. 61/551,822, filed on Oct. 26, 2011.

(51) Int. Cl.
*C12N 7/04* (2006.01)
*C12N 13/00* (2006.01)
(Continued)

(52) U.S. Cl.
CPC .................. *G01N 1/30* (2013.01); *A61L 2/10* (2013.01); *B01D 15/24* (2013.01); *C07K 1/16* (2013.01); *C07K 1/22* (2013.01)

(58) Field of Classification Search
None
See application file for complete search history.

(56) References Cited

U.S. PATENT DOCUMENTS 5,981,163 A 11/1999 Horowitz et al.
2003/0064001 A1 4/2003 Fries et al.
(Continued)

FOREIGN PATENT DOCUMENTS

EP 1415669 A1 5/2004
JP H07-058031 A 3/1995
(Continued)

OTHER PUBLICATIONS

Chin et al., "Virucidal Short Wavelength Ultraviolet Light Treatment of Plasma and Factor VIII Concentrate: Protection of Proteins by Antioxidants," Blood, vol. 86, No. 11: 4331-4336 (1995).*
(Continued)

*Primary Examiner* — M Franco G Salvoza
(74) *Attorney, Agent, or Firm* — Susan E. Lingenfelter

(57) ABSTRACT

Methods of inactivation of a virus in a sample comprising a protein component are provided. Also provided are methods of reducing protein degradation or modification in to the presence of a reactive species, such as a reactive species generated as a result of UV exposure, are also provided. In another aspect, a method of reducing oxidation of methionine residues, tryptophan residues or both methionine and tryptophan residues in a protein subjected to UV light is provided. The disclosed methods can be performed at any scale and can be automated as desired.

34 Claims, 16 Drawing Sheets

(51) Int. Cl.

| | |
|---|---|
| ***G01N 1/30*** | (2006.01) |
| ***A61L 2/10*** | (2006.01) |
| *B01D 15/24* | (2006.01) |
| *C07K 1/22* | (2006.01) |
| *C07K 1/16* | (2006.01) |

(56) References Cited

U.S. PATENT DOCUMENTS

| | | | | |
|---|---|---|---|---|
| 2003/0161753 | A1 | 8/2003 | MacPhee et al. | |
| 2003/0229212 | A1* | 12/2003 | Fahrner | C07K 1/18 530/417 |
| 2005/0264236 | A1 | 12/2005 | Lloyd et al. | |
| 2006/0045796 | A1* | 3/2006 | Anderle | A23L 3/26 422/3 |
| 2010/0068210 | A1* | 3/2010 | Ji | A61K 9/0019 514/1.1 |
| 2010/0203610 | A1* | 8/2010 | Zhou | A61L 2/0017 435/173.1 |
| 2010/0253934 | A1* | 10/2010 | D'Ascenzi | A61K 39/095 356/51 |
| 2010/0260766 | A1* | 10/2010 | Srivastava | C07K 16/2863 424/142.1 |
| 2011/0020406 | A1* | 1/2011 | Delputte | A61K 39/12 424/281.1 |

FOREIGN PATENT DOCUMENTS

| | | | | |
|---|---|---|---|---|
| JP | 11-286453 | A | 10/1999 | |
| WO | 94/28120 | A1 | 12/1994 | |
| WO | 97/43915 | A1 | 11/1997 | |
| WO | 00/20045 | A1 | 4/2000 | |
| WO | 01/26576 | A1 | 4/2001 | |
| WO | 01/70279 | A1 | 9/2001 | |
| WO | 02/092138 | A1 | 11/2002 | |
| WO | 02/096471 | A2 | 12/2002 | |
| WO | 02/103029 | A2 | 12/2002 | |
| WO | WO-03007998 | A1 * | 1/2003 | A61L 2/0011 |
| WO | 03/026704 | A1 | 4/2003 | |
| WO | 2003/026705 | A1 | 4/2003 | |
| WO | 2011/004285 | A1 | 1/2011 | |

OTHER PUBLICATIONS

Marx, G., et al., "Protecting fibrinogen with rutin during UVC irradiation for viral inactivation," Photochem. and Photobiol., vol. 63, No. 4, pp. 541-546 (1996).

Chin, S. et al., "Virucidal short wavelength ultraviolet light treatment of plasma and factor VIII concentrate: protection of proteins by antioxidants," Blood, vol. 86, No. 11, pp. 4331-4336 (1995).

Nakane, Tomohiro, Translation of Notice of Rejection, 1st Official Action, Japanese Patent Application No. 2014-539012, dated Jul. 28, 2015.

Horowitz et al. (Nov. 19, 2004), "Annex 4: Guidelines on viral inactivation and removal procedures intended to assure the viral safety of human blood plasma products", WHO Technical Report, Series No. 924:150-224.

Translation of Re-examination Report, Japanese Patent Application No. 2014-539012, Drafting Date Dec. 27, 2016.

* cited by examiner

All Molecules pH MP % Change SEC
% Change
0
-5
-10
-15
-20
-25
1
10
100
1000
mJ
Mab Z FVIP Main pH 4.3
Mab X FVIP Main pH 4.3
Mab Y FVIP Main pH 4.3
Mab Z FVIP Main pH 7.0
Mab X FVIP Main pH 7.0
Mab Y FVIP Main pH 7.0
Mab Z FVIP pH 5.0
Mab X FVIP Main pH 5.0
Mab Y FVIP Main pH 5.0

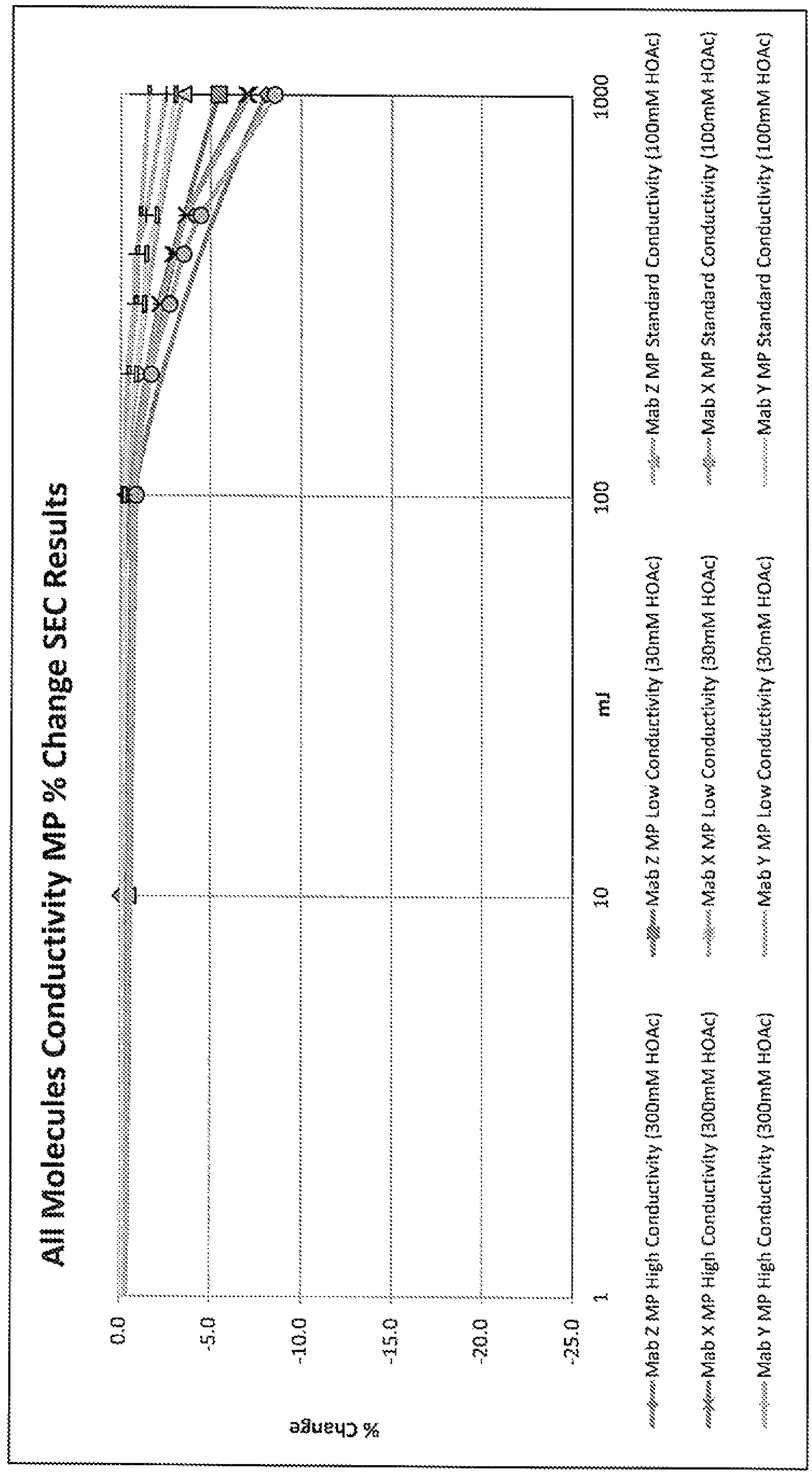
Figure 3
All Molecules Conductivity MP % Change SEC Results
% Change
0.0
-5.0
-10.0
-15.0
-20.0
-25.0
1
10
100
1000
mL
Mab Z MP High Conductivity (300mM HOAc)
Mab Z MP Low Conductivity (30mM HOAc)
Mab Z MP Standard Conductivity (100mM HOAc)
Mab X MP High Conductivity (300mM HOAc)
Mab X MP Low Conductivity (30mM HOAc)
Mab X MP Standard Conductivity (100mM HOAc)
Mab Y MP High Conductivity (300mM HOAc)
Mab Y MP Low Conductivity (30mM HOAc)
Mab Y MP Standard Conductivity (100mM HOAc)

Mab X Peptide Map UV Exposure
MP Purity
100
90
80
70
60
50
40
30
20
10
0
1
10
100
1000
10000
mJ
Peptide Map UV Exposure Run 1
Expon. (Peptide Map UV Exposure Run 1)
Peptide Map UV Exposure Run 2
Expon. (Peptide Map UV Exposure Run 2)
125 mJ
1000 mJ
10,000 mJ

Figure 8

| Peptide Mapping Results | | | | |
|---|---|---|---|---|
| | Control (0mj) | Medium (~15mJ) | High (~150mJ) | Extreme (~1000mJ) |
| Met-249 Ox | 2.4% | 2.9% | 6.8% | 35.6% |
| Met-425 Ox | 1.1% | 1.4% | 4.2% | 29.3% |

| In-vitro BioActivity | |
|---|---|
| Sample ID | % Relative Potency |
| Control (0mJ) | 86 |
| Control (125mJ) | 86 |
| Control (375mJ) | 86 |
| Control w/ Add 1 (0mJ) | 89 |
| Control w/ Add 1 (125mJ) | 87 |
| Control w/ Add 1 (375mJ) | 89 |

Mab X Peptide Map UV Exposure
MP Purity
100
90
80
70
60
50
40
30
20
10
0
1
10
100
1000
10000
mJ
Peptide Map UV Exposure Run 1
Peptide Map UV Exposure with Add.#2
Expon. (Peptide Map UV Exposure Run 2)
Peptide Map UV Exposure Run 2
Expon. (Peptide Map UV Exposure Run 1)
Expon. (Peptide Map UV Exposure with Add.#2)

Figure 11a

Literature Reference for Required UV-C Doses for Inactivation – DNA viruses

| Family[a] | Measured $UV_{254}$ $D_{37}$ ($J/m^2$)[b] | Genome size range[c] | Measured or predicted SnS ($J/m^2 \cdot kb$)[d] | Representative virus(es)[e] | Predicted $UV_{254}$ $D_{37}$ range for entire family ($J/m^2$)[f] |
|---|---|---|---|---|---|
| dsDNA viruses | | | | | |
| *Adenoviridae* | 130 (100–220) | 26–45 | 9,200 (7,300–16,000) | SAdV-7, HAdV-5, -40, -41 | 100–180 |
| *Asfarviridae* | | 170–190 | *3,100 p* | | *13–15* |
| *Herpesviridae* | 19 (6.2–28)<br>2nd 140[g]<br>(38–490) | 125–240 | 6,400 (1,600–9,600)<br>2nd 54,000[g]<br>(12,000–120,000) | HHV-1, -2, -5, SuHV-1, MuHV-1, EHV-1 | 13–26<br>2nd 110–220[g] |
| *Iridoviridae* | 16 | 98–170 | 3,100 | FV-3 | 15–26 |
| *Papillomaviridae* | | 6.8–8.4 | *5,100 p* | | *300–380* |
| *Polyomaviridae* | 250 | 4.7–5.3 | 2,600 | MPyV, SV40 | 250–280 |
| *Poxviridae* | 11 | 130–300 | 4,100 | VACV | 6.8–16 |
| ssDNA viruses | | | | | |
| *Circoviridae* | | 1.8–2.3 | *46 p* | | *20–26* |
| *Hepadnaviridae* | | 3.0–3.3 | *46 p* | | *14–15* |
| *Parvoviridae* | 9.2 (8.6–10.0) | 4–6 | 46 (43–50) | KRV, MMV, H-1PV | 7.7–12 |

Figure 11b

Literature Reference for Required UV-C Doses for Inactivation – RNA viruses

| Family[a] | Measured $D_{37}$ ($J/m^2$) | Genome size range | Measured or predicted SnS ($J/m^2 \cdot kb$) | Representative virus(es) | Predicted $D_{37}$ range for entire family ($J/m^2$) |
|---|---|---|---|---|---|
| dsRNA viruses | | | | | |
| *Birnaviridae* | 130 (110–170) | 5.7–6.2 | 1,400 (1,300–1,900) | IPNV | 110–120 |
| *Reoviridae* | 69 (46–123) | 18.6–26.4 | 3,800 (1,700–5,800) | MRV-1, -2, -3, RV-A, KEMV-10, -91 | 72–100 |
| ssRNA viruses | | | | | |
| *Arenaviridae** | | 11 | *140 p* | | *13* |
| *Bornaviridae** | 34 | 8.9 | 300 | BDV | 34 |
| *Bunyaviridae** | | 11–19 | *140 p* | | *7.4–13* |
| *Deltavirus** | | 1.7 | *140 p* | | *82* |
| *Filoviridae** | | 19 | *140 p* | | *7.4* |
| *Orthomyxoviridae** | 7.5 (4.8–40) | 10–13 | 110 (70–140) | FLUAV, ISAV | 7.3–11 |
| *Paramyxoviridae** | 11 (10–12) | 15–16 | 170 (150–190) | NDV, MeV | 11 |
| *Rhabdoviridae** | 4.3 (1.1–23) | 11–15 | 51 (12–260) | VSV, RABV, VHSV | 3.4–4.6 |
| *Arteriviridae*** | | 13–16 | *295 p* | | *18–23* |
| *Astroviridae*** | | 6.8–7.9 | *295 p* | | *37–44* |
| *Caliciviridae*** | | 7.4–8.3 | *295 p* | | *36–40* |
| *Coronaviridae*** | 3.1 | 20–31 | 78 | BEV | 2.5–3.9 |
| *Flaviviridae*** | | 9.6–12 | *295 p* | | *25–31* |
| "HEV-like" viruses** | | 7.2 | *295 p* | | *41* |
| *Nodaviridae*** | 140 | 4.5 | 630 | SBNN | 140 |
| *Picornaviridae*** | 48 (25–70) | 7–8.5 | 370 (190–540) | PV-1, -2, -3, E-1, -11, CV-A9, -B1, -B5, HHAV, EMCV | 44–53 |
| *Togaviridae*** | 19 (7.3–23) | 9–12 | 220 (83–260) | SINV, VEEV, SFV | 18–24 |
| *Retroviridae**** | 89 (88–120) | 7–11 | 740 (620–980) | MLV, FeLV, MoMSV, RSV | 67–110 |

Figure 12

Predicted LRV vs. Dose

| Virus Family | Sensitivity | Measured UV254 D37 (J/m2) | Calculated UV254 4LRV (J/m2) | Calculated UV254 6LRV (J/m2) | Calculated UV254 8LRV (J/m2) | Calculated UV254 12LRV (J/m2) | Calculated UV254 4LRV (mJ/cm2) | UV254 6LRV (mJ/cm2) | Calculated UV254 8LRV (mJ/cm2) | Calculated UV254 12LRV (mJ/cm2) |
|---|---|---|---|---|---|---|---|---|---|---|
| *Adenoviridae* | *Low* | 220 | 2024 | 3036 | 4048 | 6072 | 202.4 | 303.6 | 404.8 | 607.2 |
| | *Median* | 130 | 1196 | 1794 | 2392 | 3588 | 119.6 | 179.4 | 239.2 | 358.8 |
| | *High* | 100 | 920 | 1380 | 1840 | 2760 | 92 | 138 | 184 | 276 |
| *Polyomaviridae* | *Median* | 250 | 2300 | 3450 | 4600 | 6900 | 230 | 345 | 460 | 690 |
| *Parvoviridae* | *Low* | 10 | 92 | 138 | 184 | 276 | 9.2 | 13.8 | 18.4 | 27.6 |
| *Minute virus of mice* | *Median* | 9.2 | 84.64 | 126.96 | 169.28 | 253.92 | 8.464 | 12.696 | 16.928 | 25.392 |
| *(MVM)* | *High* | 8.6 | 79.12 | 118.68 | 158.24 | 237.36 | 7.912 | 11.868 | 15.824 | 23.736 |
| *Retroviridae (muLV)* | *Low* | 120 | 1104 | 1656 | 2208 | 3312 | 110.4 | 165.6 | 220.8 | 331.2 |
| | *Median* | 89 | 818.8 | 1228.2 | 1637.6 | 2456.4 | 81.88 | 122.82 | 163.76 | 245.64 |
| | *High* | 88 | 809.6 | 1214.4 | 1619.2 | 2428.8 | 80.96 | 121.44 | 161.92 | 242.88 |
| *Bunyaviridae* | *Low* | 13 | 119.6 | 179.4 | 239.2 | 358.8 | 11.96 | 17.94 | 23.92 | 35.88 |
| *Cache Valley Virus* | *Median* | 10.2 | 93.84 | 140.76 | 187.68 | 281.52 | 9.384 | 14.076 | 18.768 | 28.152 |
| *(CVV)* | *High* | 7.4 | 68.08 | 102.12 | 136.16 | 204.24 | 6.808 | 10.212 | 13.616 | 20.424 |

ln(n/no) = (-kD)
k = 1/(D37)
$\log_{10}(x) = \{\log_e(x) / \log_e(10)\}$
$\log_{10}(x) = \{\ln(x) / 2.3\}$
LRV = - log10(n/no) = - {ln(n/no) / 2.3} = (1/2.3)*(D/D37)
D = 2.3 * D37 * LRV n0=100
D=received dose
n/no=% undamaged
Curve: x=-log10(n/no), y= dose
Slope=(-1/2.3)*1/D37=(-D37/2.3)
= - log10(n/no) = (1/2.3)*(D/D37)
D37=(1/slope)*(-1/2.3)=(-slope/2.3)
Protection Factor=D37 treated/D37untreated

METHODS OF REDUCING OR ELIMINATING PROTEIN MODIFICATION AND DEGRADATION ARISING FROM EXPOSURE TO UV LIGHT

CROSS REFERENCE TO RELATED APPLICATIONS

This application is a national stage application under 35 U.S.C. § 371 of International Application No. PCT/US2012/061965, having an international filing date of Oct. 25, 2012; which claims priority to U.S. Provisional Patent Application No. 61/551,822, filed Oct. 26, 2011, which is incorporated herein by reference.

FIELD OF THE INVENTION

The present invention relates generally to compounds and processes for protecting protein-based molecules from degradation and modification during operations involving exposure of the protein-based molecules to UV light, particularly viral inactivation processes using light in the UV-C wavelengths, and for facilitating increased UV-C exposure without damage to the proteins.

BACKGROUND OF THE INVENTION

Viral contamination of cellular media and supernatants poses a challenge to biopharmaceutical manufacturers worldwide. Several methods have been employed to inactivate and/or remove large or small, enveloped or non-enveloped (or "naked") DNA or RNA viral particles from cellular supernatants. Examples of these approaches include 20 nm filtration technology, anion-exchange membrane chromatography, low pH incubation and depth filter technology.

In addition to the above techniques, ultraviolet light has also been used to treat protein-containing solutions in order to inactivate viruses. In order to achieve efficient viral inactivation, however, the solution must be exposed to a sufficient dose of UV light, in the UV-C band. In some instances, the desired level of UV-C light exposure can cause undesirable modification and/or degradation of the protein in the solution. For example, in some cases reactive species may form in the solution and result in indirect oxidation or modification of proteins in the solution; other mechanisms for indirect modification due to UV-C exposure are also possible. See, e.g., Cabiscol, et al., (2010) *Int. Microbiol,* 3:315; Bandyopadhyay et al. (1999) *Curr. Sci.* 77:658-666; Schoneich, (2005) *Biochim Biophys Acta* 1703:111-19; Stadtman et al., (2003) *Antioxid. Redox. Signal* 5:577-82; Stadtman, (1993) *Ann. Rev. Biochem.* 62:797-821; and Dean et al., (1997) *Biochem. J.* 324:1-18.

The present disclosure addresses these and other challenges by providing methods of reducing oxidation, modification and degradation of protein in a solution exposed to UV band light, and more particularly UV-C light. Exposure to UV-C can be, as described, a component of a viral inactivation operation, and the protein in the solution can be of any type, for example a protein such as an antigen binding protein (e.g., one or more of (i) an antigen binding protein comprising one or more of a monoclonal antibody, a human antibody, a humanized antibody, a chimeric antibody, a recombinant antibody, a single chain antibody, a diabody, a triabody, a tetrabody, a Fab fragment, a $F(ab')_2$ fragment, an IgD antibody, an IgE antibody, an IgM antibody, an IgG1 antibody, an IgG2 antibody, an IgG3 antibody, or an IgG4 antibody, and fragments thereof, (ii) an Fc domain; (iii) a peptide; (iv) an Fc fusion protein; and (v) a therapeutic protein).

SUMMARY OF THE INVENTION

In one aspect a method of inactivating a virus in a sample comprising a protein component is provided. In one embodiment the method comprises (a) providing a sample comprising a protein component, wherein the sample is known or suspected to contain a virus; (b) identifying a target dose of UV light under which the virus is inactivated; (c) adding a protectant to the sample to form a stabilized mixture; (d) exposing the stabilized mixture to UV light provided by a source operating at a selected power level and selected wavelength for a selected period of time; (e) assessing the UV-C exposure level of the stabilized mixture; and (f) modulating one or more of the wavelength, the UV light source power and the UV light exposure time if the assessment indicates the target dose of UV light has not been delivered to the stabilized mixture.

In one embodiment the sample comprises a chromatography column pool; in specific embodiments the pool can comprise one or more of a Protein A column eluant pool comprising the protein component, a Protein G column eluant pool comprising the protein component, a HIC column pool comprising the protein component, a SEC column pool comprising the protein component, an IEC column pool comprising the protein component, and a hydroxyapatite column pool comprising the protein component. In another embodiment the sample comprises a chromatography column effluent stream; in specific embodiments the effluent stream can comprise one or more of a Protein A column effluent stream comprising the protein component, a Protein G column effluent stream comprising the protein component, a HIC column effluent stream comprising the protein component, a SEC column effluent stream comprising the protein component, an IEC column effluent stream comprising the protein component, and a hydroxyapatite column effluent stream comprising the protein component.

In other embodiments the protein component can comprise one or more of (i) an antigen binding protein comprising one or more of a monoclonal antibody, a human antibody, a humanized antibody, a chimeric antibody, a recombinant antibody, a single chain antibody, a diabody, a triabody, a tetrabody, a Fab fragment, a $F(ab')_2$ fragment, an IgD antibody, an IgE antibody, an IgM antibody, an IgG1 antibody, an IgG2 antibody, an IgG3 antibody, or an IgG4 antibody, and fragments thereof, (ii) an Fc domain; (iii) a peptide; (iv) an Fc fusion protein; and (v) a therapeutic protein. In still further embodiments the virus comprises one or more of a dsDNA virus, a ssDNA virus, a dsRNA virus and a ssRNA virus; in specific embodiments the virus can comprise a virus of one or more of the virus families adenoviridae, asfarviridae, herpesviridae, iridoviridae, papillomaviridae, polyomaviridae, poxviridae, circoviridae, hepadnaviridae, parvoviridae, birnaviridae, reoviridae, arenaviridae, vornaviridae, bunyaviridae, deltaviridae, filoviridae, orthomyxoviridae, paramyxoviridae, rhabdoviridae, arterioviridae, astroviridae, caliciviridae, cornonavirdae, flaviviridae, HEV-like viruses, nodaviridae, picornaviridae, togaviridae, and tertroviridae. In particular embodiments the virus is the parvovirus MVM, the retrovirus MuLV or the bunya virus CVV.

In yet another embodiment the protectant is added to the sample in a concentration ratio of greater than 1 part protectant to 200 parts protein and in other embodiments the protectant can comprise one or more of tyrosine, tryptophan, methionine, pyridoxine and riboflavin. In specific embodiments the protectant comprises one of (i) tyrosine; (ii) tryptophan; and (iii) tyrosine and tryptophan.

In still further embodiments the UV light has a wavelength in the range of about 200 nm to about 280 nm; in specific embodiments the UV light has a wavelength of about 254 nm. The target dose, in various embodiments, can be one or more of about 1 $mJ/cm^2$, about 10 $mJ/cm^2$, about 25 $mJ/cm^2$, about 50 $mJ/cm^2$, about 75 $mJ/cm^2$, about 100 $mJ/cm^2$, about 125 $mJ/cm^2$, about 200 $mJ/cm^2$, about 250 $mJ/cm^2$, about 300 $mJ/cm^2$, about 350 $mJ/cm^2$, about 400 $mJ/cm^2$, about 450 $mJ/cm^2$, about 500 $mJ/cm^2$, about 600 $mJ/cm^2$, about 700 $mJ/cm^2$, about 800 $mJ/cm^2$, about 900 $mJ/cm^2$, about 1000 $mJ/cm^2$ and greater than about 1000 $mJ/cm^2$.

In some embodiments the method provides a viral log reduction value (LRV) of greater than or equal to about 0.5, about 1.0, about 1.5, about 2.0, about 2.5, about 3.0, about 3.5, about 4.0, about 4.5, about 5.0, about 5.5, about 6.0, about 6.5 or greater than about 6.5.

In another embodiment the method is automated and in still another embodiment the method is performed as a step in a protein purification operation.

In another aspect, a method of reducing protein degradation or modification arising from the presence of a reactive species generated during UV exposure is provided. In one embodiment the method comprises (a) providing a sample comprising a protein component known or suspected to be degraded or modified in the presence of a reactive species; (b) identifying a target dose of UV light; (c) adding a protectant to the sample to form a stabilized mixture; (d) exposing the stabilized mixture to UV light provided by a source operating at a selected power level and selected wavelength for a selected period of time; (e) assessing the UV-C exposure level of the stabilized mixture; and (f) modulating one or more of the wavelength, the UV light source power and the UV light exposure time if the assessment indicates the target dose of UV light has not been delivered to the stabilized mixture.

In one embodiment the sample comprises a chromatography column pool; in specific embodiments the pool can comprise one or more of a Protein A column eluant pool comprising the protein component, a Protein G column eluant pool comprising the protein component, a HIC column pool comprising the protein component, a SEC column pool comprising the protein component, an IEC column pool comprising the protein component, and a hydroxyapatite column pool comprising the protein component. In another embodiment the sample comprises a chromatography column effluent stream; in specific embodiments the effluent stream can comprise one or more of a Protein A column effluent stream comprising the protein component, a Protein G column effluent stream comprising the protein component, a HIC column effluent stream comprising the protein component, a SEC column effluent stream comprising the protein component, an IEC column effluent stream comprising the protein component, and a hydroxyapatite column effluent stream comprising the protein component.

In other embodiments the protein component can comprise one or more of (i) an antigen binding protein comprising one or more of a monoclonal antibody, a human antibody, a humanized antibody, a chimeric antibody, a recombinant antibody, a single chain antibody, a diabody, a triabody, a tetrabody, a Fab fragment, a $F(ab')_2$ fragment, an IgD antibody, an IgE antibody, an IgM antibody, an IgG1 antibody, an IgG2 antibody, an IgG3 antibody, or an IgG4 antibody, and fragments thereof, (ii) an Fc domain; (iii) a peptide; (iv) an Fc fusion protein; and (v) a therapeutic protein.

In yet another embodiment the protectant is added to the sample in a concentration ratio of greater than 1 part protectant to 200 parts protein and in other embodiments the protectant can comprise one or more of tyrosine, tryptophan, methionine, pyridoxine and riboflavin. In specific embodiments the protectant comprises one of (i) tyrosine; (ii) tryptophan; and (iii) tyrosine and tryptophan.

In still further embodiments the UV light has a wavelength in the range of about 200 nm to about 280 nm; in specific embodiments the UV light has a wavelength of about 254 nm. The target dose, in various embodiments can be one or more of about 1 $mJ/cm^2$, about 10 $mJ/cm^2$, about 25 $mJ/cm^2$, about 50 $mJ/cm^2$, about 75 $mJ/cm^2$, about 100 $mJ/cm^2$, about 125 $mJ/cm^2$, about 200 $mJ/cm^2$, about 250 $mJ/cm^2$, about 300 $mJ/cm^2$, about 350 $mJ/cm^2$, about 400 $mJ/cm^2$, about 450 $mJ/cm^2$, about 500 $mJ/cm^2$, about 600 $mJ/cm^2$, about 700 $mJ/cm^2$, about 800 $mJ/cm^2$, about 900 $mJ/cm^2$, about 1000 $mJ/cm^2$ and greater than about 1000 $mJ/cm^2$.

In some embodiments the method provides a viral log reduction value (LRV) of greater than or equal to about 0.5, about 1.0, about 1.5, about 2.0, about 2.5, about 3.0, about 3.5, about 4.0, about 4.5, about 5.0, about 5.5, about 6.0, about 6.5 or greater than about 6.5.

In another embodiment the method is automated and in still another embodiment the method is performed as a step in a protein purification operation.

In still another aspect, a method of reducing oxidation of methionine residues, tryptophan residues or both methionine and tryptophan residues in a protein subjected to UV light is provided. In one embodiment the method comprises (a) providing a sample comprising a protein component comprising a methionine residue, a tryptophan residue or both a methionine and a tryptophan residue; (b) identifying a target dose of UV light; (c) adding a protectant to the sample to form a stabilized mixture; (d) exposing the stabilized mixture to UV light provided by a source operating at a selected power level and selected wavelength for a selected period of time; (e) assessing the UV-C exposure level of the stabilized mixture; and (f) modulating one or more of the wavelength, the UV light source power and the UV light exposure time if the assessment indicates the target dose of UV light has not been delivered to the stabilized mixture.

In one embodiment the sample comprises a chromatography column pool; in specific embodiments the pool can comprise one or more of a Protein A column eluant pool comprising the protein component, a Protein G column eluant pool comprising the protein component, a HIC column pool comprising the protein component, a SEC column pool comprising the protein component, an IEC column pool comprising the protein component, and a hydroxyapatite column pool comprising the protein component. In another embodiment the sample comprises a chromatography column effluent stream; in specific embodiments the effluent stream can comprise one or more of a Protein A column effluent stream comprising the protein component, a Protein G column effluent stream comprising the protein component, a HIC column effluent stream comprising the protein component, a SEC column effluent stream comprising the protein component, an IEC column effluent stream comprising the protein component, and a hydroxyapatite column effluent stream comprising the protein component.

In other embodiments the protein component can comprise one or more of (i) an antigen binding protein comprising one or more of a monoclonal antibody, a human antibody, a humanized antibody, a chimeric antibody, a recombinant antibody, a single chain antibody, a diabody, a triabody, a tetrabody, a Fab fragment, a $F(ab')_2$ fragment, an IgD antibody, an IgE antibody, an IgM antibody, an IgG1 antibody, an IgG2 antibody, an IgG3 antibody, or an IgG4 antibody, and fragments thereof, (ii) an Fc domain; (iii) a peptide; (iv) an Fc fusion protein; and (v) a therapeutic protein.

In yet another embodiment the protectant is added to the sample in a concentration ratio of greater than 1 part protectant to 200 parts protein and in other embodiments the protectant can comprise one or more of tyrosine, tryptophan, methionine, pyridoxine and riboflavin. In specific embodiments the protectant comprises one of (i) tyrosine; (ii) tryptophan; and (iii) tyrosine and tryptophan.

In still further embodiments the UV light has a wavelength in the range of about 200 nm to about 280 nm; in specific embodiments the UV light has a wavelength of about 254 nm. The target dose, in various embodiments can be one or more of about 1 mJ/cm$^2$, about 10 mJ/cm$^2$, about 25 mJ/cm$^2$, about 50 mJ/cm$^2$, about 75 mJ/cm$^2$, about 100 mJ/cm$^2$, about 125 mJ/cm$^2$, about 200 mJ/cm$^2$, about 250 mJ/cm$^2$, about 300 mJ/cm$^2$, about 350 mJ/cm$^2$, about 400 mJ/cm$^2$, about 450 mJ/cm$^2$, about 500 mJ/cm$^2$, about 600 mJ/cm$^2$, about 700 mJ/cm$^2$, about 800 mJ/cm$^2$, about 900 mJ/cm$^2$, about 1000 mJ/cm$^2$ and greater than about 1000 mJ/cm$^2$.

In some embodiments the method provides a viral log reduction value (LRV) of greater than or equal to about 0.5, about 1.0, about 1.5, about 2.0, about 2.5, about 3.0, about 3.5, about 4.0, about 4.5, about 5.0, about 5.5, about 6.0, about 6.5 or greater than about 6.5.

In another embodiment the method is automated and in still another embodiment the method is performed as a step in a protein purification operation.

BRIEF DESCRIPTION OF THE DRAWINGS

FIG. 3 is a plot of percent main peak change in three different monoclonal antibody samples (Mab X, Mab Y, Mab Z) as a function of UV-C exposure monitored at three different conductivity levels (Low (30 mM HOAc), Standard (100 mM HOAc), and High (300 mM HOAc)) by SEC-HPLC assay; the y-axis is plotted as % change in value compared to 0 mJ/cm$^2$ dose delivered to the solution surface and the x-axis is plotted as calculated dose (mJ/cm$^2$) delivered to the solution surface.

FIG. 8 is a table summarizing purity and activity trends for a monoclonal antibody (Mab X) as a function of UV-C exposure doses of 0, 150, 375 and/or 1000 mJ/cm$^2$. The peptide map results identify oxidation of specific methionine residues on the protein that increase in level with increasing dose. Mab X is referred to as "Control" and tyrosine is referred to as "Add 1".

FIGS. 11*a* and 11*b* are tables showing required UV-C doses required for inactivation of DNA viruses (FIG. 11*a*) and RNA viruses (FIG. 11*b*).

FIG. 12 is a table showing predicted log reduction value (LRV) versus UV dose required for inactivation of various viruses.

DETAILED DESCRIPTION OF THE INVENTION

Figure 1:
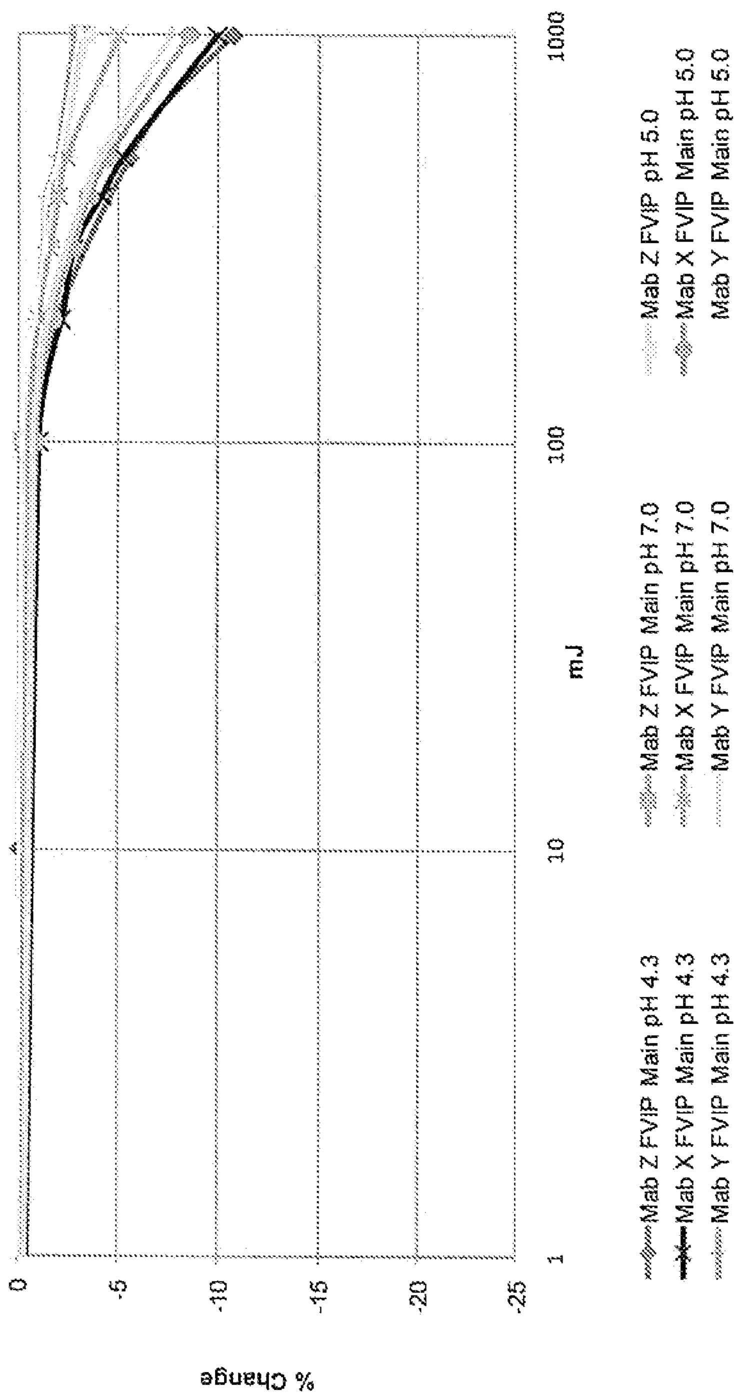
FIG. 1 is a plot of percent main peak changes in three different monoclonal antibody samples (Mab X, Mab Y, Mab Z) as a function of UV-C exposure monitored at three different pH levels (ph 4.3, 5.0 and 7.0) by SEC-HPLC assay; the y-axis is plotted as % change in value compared to 0 mJ dose delivered to the solution surface and the x-axis is plotted as calculated dose delivered (mJ/cm$^2$) to the solution surface. All samples were filtered viral inactivated pools (FVIP).
Figure 2:
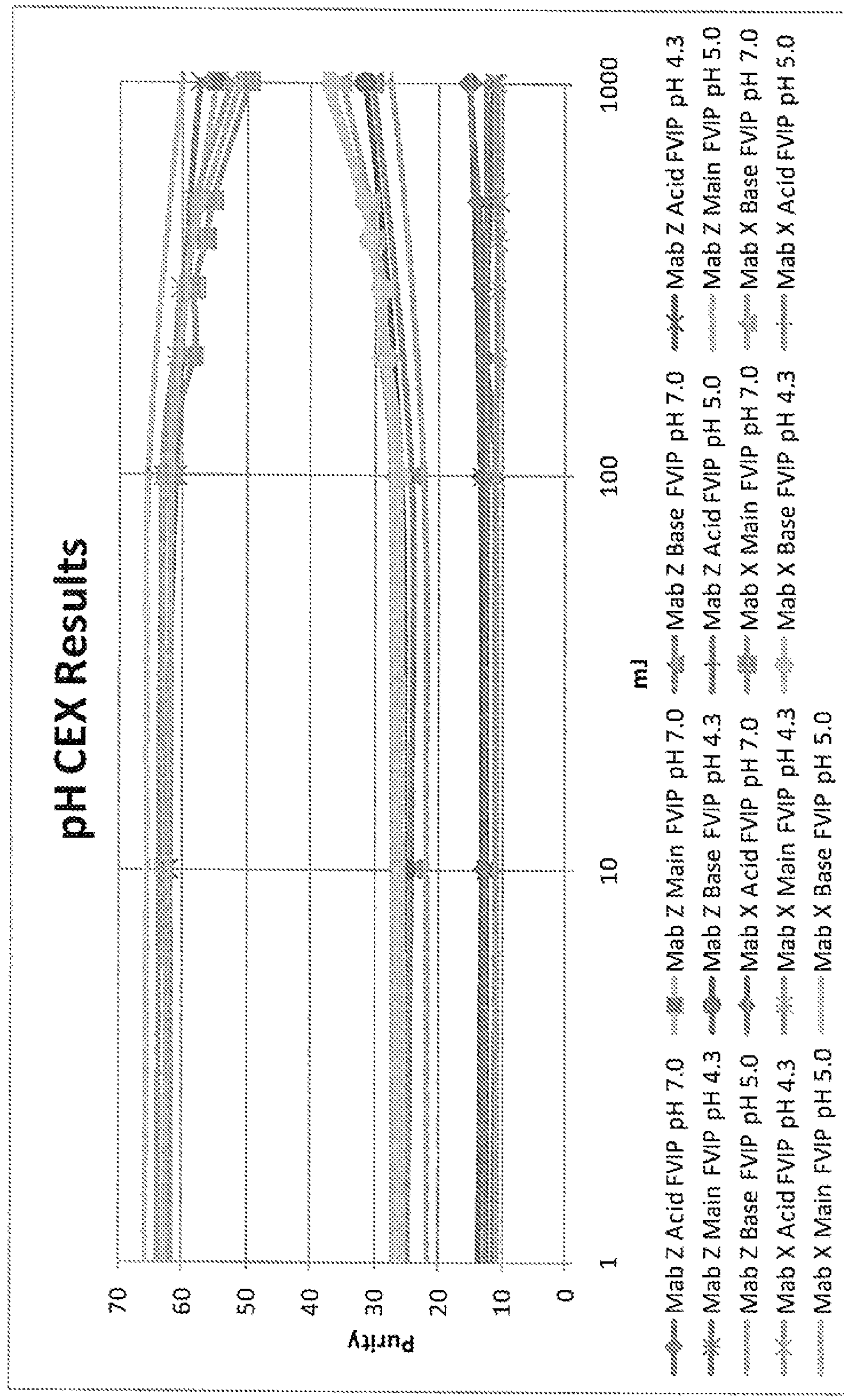
FIG. 2 is a plot of main peak, acidic peak and basic peak purity of two different monoclonal antibody samples (Mab X, Mab Z) as a function of UV-C exposure monitored at three different pH levels (pH 4.3, 5.0 and 7.0) by CEX-HPLC assay; the y-axis is plotted as % distribution of the measured species, compared to 0 mJ/cm$^2$ dose delivered to the solution surface and the x-axis is plotted as calculated dose (mJ/cm$^2$) delivered to the solution surface. All samples were filtered viral inactivated pools (FVIP).
Figure 4:
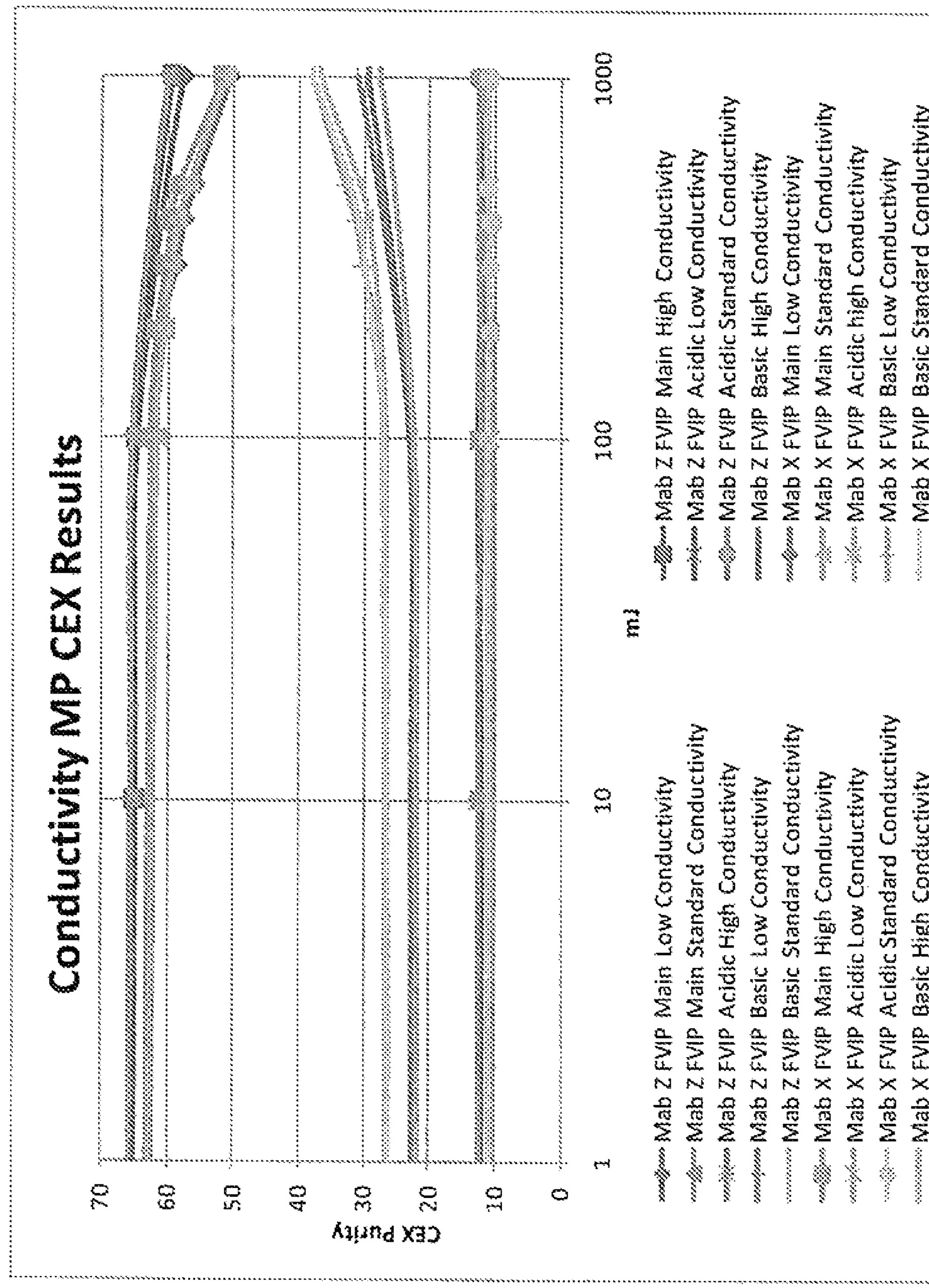
FIG. 4 is a plot of main peak, acidic peak and basic peak purity of two different monoclonal antibody samples (Mab X, Mab Z) as a function of UV-C exposure monitored at three different conductivity levels (Low (30 mM HOAc), Standard (100 mM HOAc), and High (300 mM HOAc)) by CEX-HPLC assay; the y-axis is plotted as % distribution of the measured species, compared to 0 mJ/cm$^2$ dose delivered to the solution surface and the x-axis is plotted as calculated dose (mJ/cm$^2$) delivered to the solution surface. All samples were filtered viral inactivated pools (FVIP).
Figure 5:
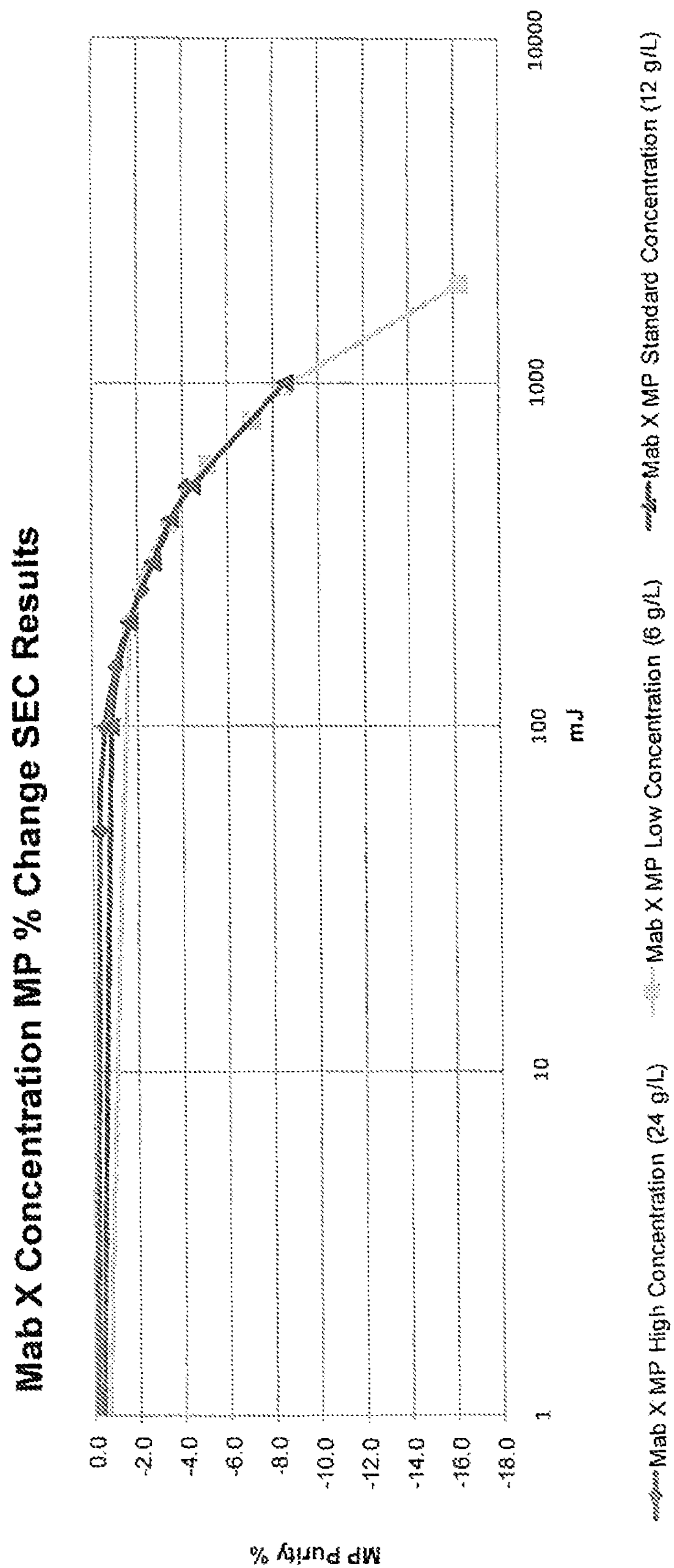
FIG. 5 is a plot of the main peak concentration of a monoclonal antibody (Mab X) as a function of UV-C exposure monitored at three different concentrations (Low (6 g/L), Standard (12 g/L), High (24 g/L)) by SEC-HPLC assay; the y-axis is plotted as % change in value compared to 0 mJ/cm$^2$ dose delivered to the solution surface and the x-axis is plotted as calculated dose (mJ/cm$^2$) received, when accounting for UV absorbance by the solution components.
Figure 6:
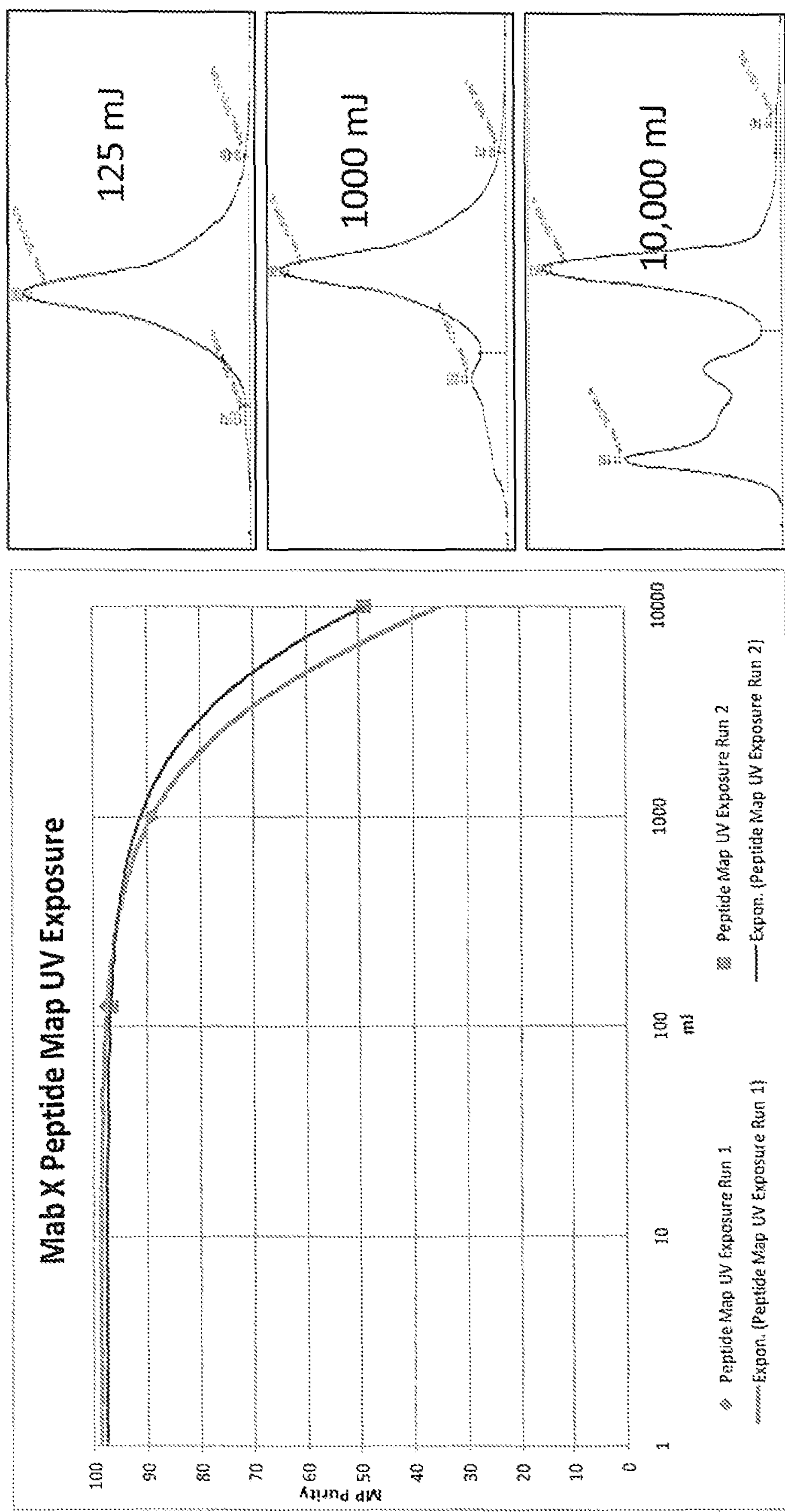
FIG. 6 is a plot and three traces of the main peak purity of a monoclonal antibody (Mab X) as a function of UV-C exposure as monitored by SEC-HPLC assay. The plot shows two peptide maps for Mab X, UV Exposure Run 1 and UV Exposure Run 2. The y-axis is plotted as % change in value compared to 0 mJ/cm$^2$ dose delivered to the solution surface and the x-axis is plotted as calculated dose (mJ/cm$^2$) delivered to the solution surface.
Figure 7:
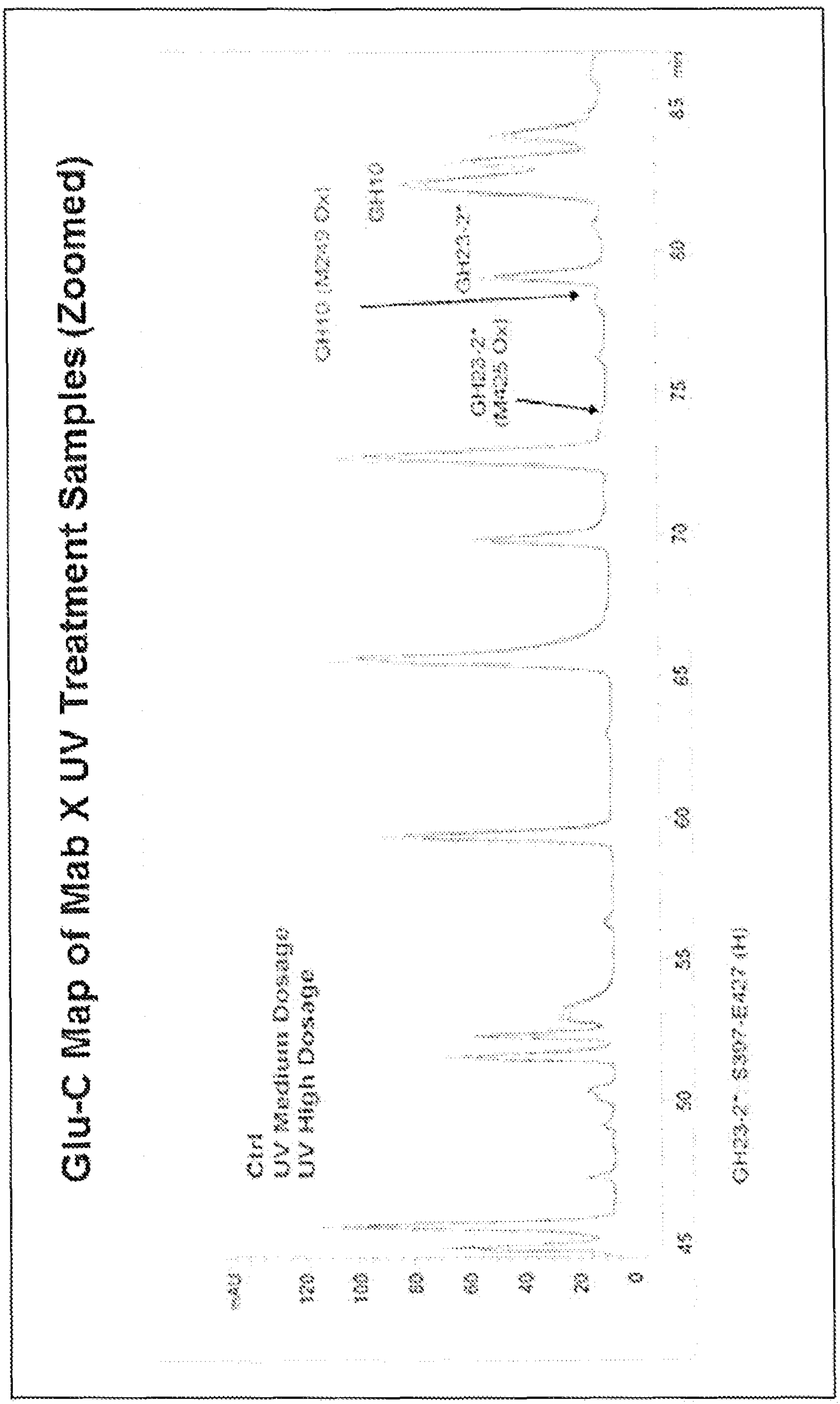
FIG. 7 is a peptide map highlighting the oxidation effects observed on amino acid residues of a monoclonal antibody (Mab X) following UV-C exposure of 10,000 mJ/cm$^2$ delivered to the solution surface. Oxidation of the methionine residues at position 425 and 249 were observed upon this extreme UV-C dose exposure.
Figure 9:
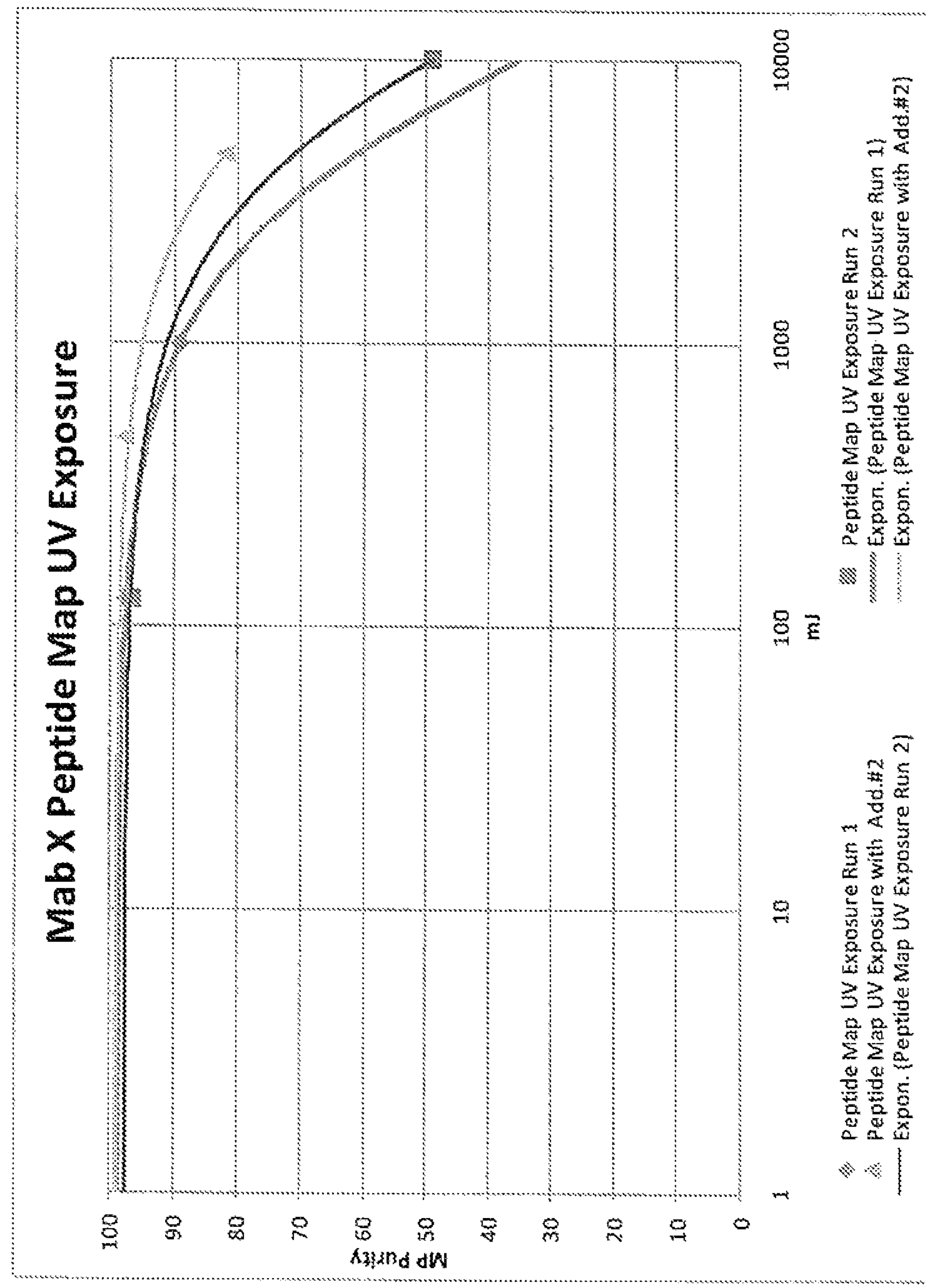
FIG. 9 is a plot of the main peak purity of a monoclonal antibody (Mab X) as a function of UV-C exposure in the presence and absence of a protectant as monitored by SEC-HPLC assay; the y-axis is plotted as % main peak, as a distribution of measured species and the x-axis is plotted as calculated dose delivered to the solution surface (mJ/cm$^2$). The plot shows three peptide maps for Mab X, UV Exposure Run 1 and UV Exposure Run 2, untreated repeat runs, and UV Exposure "Add. #2" a protected run with tryptophan.
Figure 10:
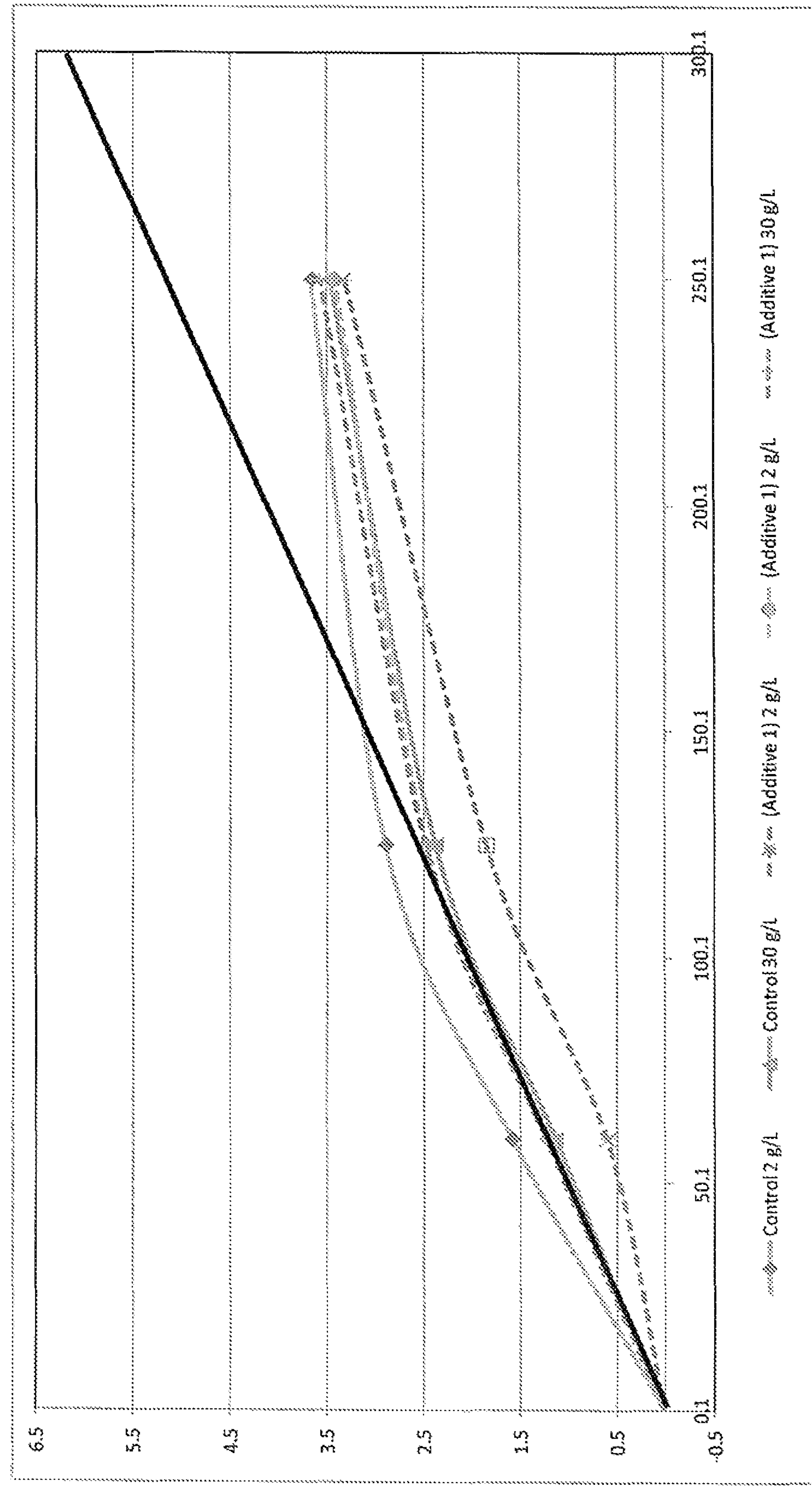
FIG. 10 is a plot of xmuLV inactivation as a function of UV-C exposure in the presence and absence of a protectant and a monoclonal antibody (Mab Y). The y-axis is plotted as relative log reduction from a known viral load spike (log reduction value (LRV)). The x-axis is plotted as calculated dose received, when accounting for UV absorbance by the solution components (mJ/cm$^2$). The protein concentration in the sample "Control" (Mab Y) is at 2 g/L and 30 g/L, the protein concentration in the sample "Additive 1" (Mab Y+tyrosine) is at 2 g/L and 30 g/L.

The instant disclosure provides methods of treating protein containing solutions with radiation in the C band of the ultraviolet light range (UV-C, approximately 254 nm). More particularly, the instant disclosure provides method of treating protein containing solutions with radiation in the C band of the ultraviolet light range (UV-C, approximately 254 nm) in the presence of chemicals that stabilize the protein or minimize protein modifications, e.g., oxidation of residues such as methionine and tryptophan.

The viral inactivation processes provided herein targets a careful balance that minimizes protein damage, modification or adulteration, while maximizing the potential to inactivation of viral and viral-related particles. The instant disclosure provides the identities of various solution additives that may provide protection of solution proteins from indirect modification by species created upon treatment of the solution by UV-C band light. Data was collected across a number of polypeptide molecules, notably antigen binding proteins (e.g., monoclonal antibody molecules), to establish the effects of UV-C on protein modification. A relationship was established between dose level (mJ of UV-C transmitted/$cm^2$) and the level of protein modification, as measured by SEC-HPLC (to examine aggregation and dimerization), CEX-HPLC (to examine charge modification), peptide mapping (to examine molecular modification, oxidation and other effects), and bioactivity (to examine molecular potency).

In one aspect, therefore, the present disclosure relates to a method of inactivating a virus in a sample containing a protein component. The method involves the use of UV light to inactivate a virus. One beneficial aspect of the disclosed method is that it incorporates a protectant that can minimize the possibility of degradation or modification of the protein component of the sample. The method can involve a feedback component, in which a sample comprising a protectant is monitored to ensure that the sample is getting a sufficient dose of UV light to inactivate the virus but at the same time minimize exposure of the protein component to doses of UV light that can damage the protein. This process can efficiently eliminate viruses in a sample, while at the same time minimizing protein degradation and can be of benefit when working at large scales, either in terms of sample volume or in parallel operations, particularly since the method is scalable from bench scale, which involves cultures on the order of several liters, up to production scale, which involves cultures of thousands of liters.

In another aspect, the present disclosure relates to a method of reducing protein degradation or modification in the presence of a reactive species, such as a reactive species that may be generated by exposure of a solution to UV light. It has been observed that proteins can degrade or be modified as a result of prolonged exposure to UV light. By including a protectant in a sample comprising a protein component, damage to the protein can be reduced or eliminated. The method can involve a feedback component, in which a sample comprising a protectant is monitored to ensure that the sample is getting a sufficient dose of UV light to inactivate the virus but at the same time minimize exposure of the protein component to doses of UV light that can damage the protein. This process can efficiently protect the protein component of a sample from protein degradation or modification and can be of benefit when working at large scales, either in terms of sample volume or in parallel operations, particularly since the method is scalable from bench scale, which involves cultures on the order of several liters, up to production scale, which involves cultures of thousands of liters.

In still another aspect, the present disclosure relates to a method of reducing oxidation of methionine residues, tryptophan residues or both methionine and tryptophan residues in a protein subjected to UV light. It has been observed that tryptophan and methionine can oxidize as a result of prolonged exposure to UV light. By including a protectant in a sample comprising a protein component, such oxidation can be reduced or eliminated. The method can involve a feedback component, in which a sample comprising a protectant is monitored to ensure that the sample is getting a sufficient dose of UV light to inactivate the virus but at the same time minimize exposure of the protein component to doses of UV light that can damage the protein. This process can efficiently protect the protein component of a sample from protein degradation or modification and can be of benefit when working at large scales, either in terms of sample volume or in parallel operations, particularly since the method is scalable from bench scale, which involves cultures on the order of several liters, up to production scale, which involves cultures of thousands of liters.

One advantage of the disclosed methods is that they may be performed at a range of scales, from laboratory scale (typically milliliter or liter scale), a pilot plant scale (typically hundreds of liters) or on an industrial scale (typically thousands of liters). Moreover, the process can also be performed multiple times in parallel or in sequence. Accordingly, the process is readily adaptable to automation. The application of the disclosed methods on large scales may be particularly desirable in a biomolecule manufacturing process.

I. Definitions

As used herein, the terms "a" and "an" mean one or more unless specifically indicated otherwise.

As used herein, the term "antigen" refers to a molecule or a portion of a molecule capable of being bound by a selective binding agent, such as an antigen binding protein (including, e.g., an antibody or immunological functional fragment thereof), and may also be capable of being used in an animal to produce antibodies capable of binding to that antigen. An antigen can possess one or more epitopes that are capable of interacting with different antigen binding proteins, e.g., antibodies.

As used herein, the term "antigen binding protein" refers to a protein comprising a portion that binds to an antigen or target and, optionally, a scaffold or framework portion that allows the antigen binding portion to adopt a conformation that promotes binding of the antigen binding protein to the antigen. Examples of antigen binding proteins include a monoclonal antibody; a human antibody; a humanized antibody; a chimeric antibody; a recombinant antibody; a single chain antibody; a diabody; a triabody; a tetrabody; a domain antibody; a Fab fragment; a $F(ab')_2$ fragment; an IgD antibody; an IgE antibody; an IgM antibody; an IgG1 antibody; an IgG2 antibody; an IgG3 antibody; or an IgG4 antibody, and fragments thereof. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, e.g., Korndorfer et al., (2003) *Proteins: Structure, Function, and Bioinformatics,* 53(1):121-129; Roque et al., (2004) *Biotechnol. Prog.* 20:639-654. In addition, peptide antibody mimetics ("PAMs"), can form a scaffold, as well as scaffolds based on antibody mimetics utilizing fibronectin components.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* $2^{nd}$ ed. Ch. 7 (Paul, W., ed., Raven Press, N.Y. (1989)), incorporated by reference in its entirety for all purposes. The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain can be done in accordance with the definitions of Kabat et al., (1991) "Sequences of Proteins of Immunological Interest", $5^{th}$ Ed., US Dept. of Health and Human Services, PHS, NIH, NIH Publication no. 91-3242. Although presented using the Kabat nomenclature system, as desired, the CDRs disclosed herein can also be redefined according an alternative nomenclature scheme, such as that of Chothia (see Chothia & Lesk, (1987) *J. Mol. Biol.* 196:901-917; Chothia et al., (1989) *Nature* 342:878-883 or Honegger & Pluckthun, (2001) *J. Mol. Biol.* 309:657-670).

As used herein, the term "antibody" refers to an intact immunoglobulin or to an antigen binding portion thereof that competes with the intact antibody for specific binding, unless otherwise specified. Antigen binding portions can be produced by recombinant DNA techniques or by enzymatic or chemical cleavage of intact antibodies. Antigen binding portions include, inter alia, Fab, Fab', $F(ab')_2$, Fv, domain antibodies (dAbs), fragments including complementarity determining regions (CDRs), single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_H1$ domains; a $F(ab')_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, and 6,696,245; and US App. Pub. Nos. 05/0202512, 04/0202995, 04/0038291, 04/0009507, 03/0039958, Ward et al., *Nature* 341:544-546 (1989)).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., (1988) *Science* 242:423-26 and Huston et al., (1988) *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., (1993) *Proc. Natl. Acad. Sci. USA* 90:6444-48, and Poljak et al., (1994) *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody can be identified using the system described by Kabat et al., (1991) "Sequences of Proteins of Immunological Interest", $5^{th}$ Ed., US Dept. of Health and Human Services, PHS, NIH, NIH Publication no. 91-3242. Although presented using the Kabat nomenclature system, as desired, the CDRs disclosed herein can also be redefined according an alternative nomenclature scheme, such as that of Chothia (see Chothia & Lesk, (1987) *J. Mol. Biol.* 196:901-917; Chothia et al., (1989) *Nature* 342:878-883 or Honegger & Pluckthun, (2001) *J. Mol. Biol.* 309:657-670). One or more CDRs can be incorporated into a molecule either covalently or noncovalently to make it an antigen binding protein. An antigen binding protein can incorporate the CDR(s) as part of a larger polypeptide chain, can covalently link the CDR(s) to another polypeptide chain, or can incorporate the CDR(s) noncovalently. The CDRs permit the antigen binding protein to specifically bind to a particular antigen of interest.

An antigen binding protein can have one or more binding sites. If there is more than one binding site, the binding sites can be identical to one another or can be different. For example, a naturally occurring human immunoglobulin typically has two identical binding sites, while a "bispecific" or "bifunctional" antibody has two different binding sites. Antigen binding proteins of this bispecific form comprise aspects of the instant disclosure.

As used herein, the term "human antibody" refers to all antibodies that have one or more variable and constant regions derived from human immunoglobulin sequences. In one embodiment, all of the variable and constant domains are derived from human immunoglobulin sequences (a fully human antibody). These antibodies can be prepared in a variety of ways, examples of which are described below, including through the immunization with an antigen of interest of a mouse that is genetically modified to express antibodies derived from human heavy and/or light chain-encoding genes, such as a mouse derived from the use of Xenomouse® technology, UltiMab™ technology, HuMAb-Mouse® technology, Velocimouse® technology, Velocimmune® technology, KyMouse technology, or AlivaMab system, or derived from human heavy chain transgenic mouse, transgenic rat human antibody repertoire, transgenic rabbit human antibody repertoire or cow human antibody repertoire or HuTarg™ technology. Phage-based approaches can also be employed.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies can be found in U.S. Pat. Nos. 6,054,297, 5,886,152 and 5,877,293.

As used herein, the term "chimeric antibody" refers to an antibody that contains one or more regions from one antibody and one or more regions from one or more other antibodies. In one embodiment, one or more of the CDRs are derived from a human antibody that binds to a selected target. In another embodiment, all of the CDRs are derived from a human antibody that binds to a selected target. In another embodiment, the CDRs from more than one human antibody that binds to a selected target are mixed and matched in a chimeric antibody. For instance, a chimeric antibody can comprise a CDR1 from the light chain of a first human antibody that binds to a selected target, a CDR2 and a CDR3 from the light chain of a second human antibody that binds to a selected target, and the CDRs from the heavy chain from a third antibody that binds to a selected target. Further, the framework regions can be derived from one of the same antibodies that bind to a selected target, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody or antibodies from another species or belonging to another antibody class or subclass. Also included are fragments of such antibodies that exhibit the desired biological activity (e.g., the ability to specifically bind to a selected target).

As used herein, the terms "Fc" and "Fc region" are used interchangeably and refer to a fragment of an antibody that comprises human or non-human (e.g., murine) $C_{H2}$ and $C_{H3}$ immunoglobulin domains, or which comprises two contiguous regions which are at least 90% identical to human or non-human $C_{H2}$ and $C_{H3}$ immunoglobulin domains. The two heavy chain fragments are held together by two or more disulfide bonds and by hydrophobic interactions of the $C_H3$ domains. An Fc can but need not have the ability to interact with an Fc receptor. See, e.g., Hasemann & Capra, "Immunoglobulins: Structure and Function," in William E. Paul, ed., *Fundamental Immunology*, Second Edition, 209, 210-218 (1989), which is incorporated by reference herein in its entirety.

As used herein, the terms "Fc fusion" and "Fc fusion protein" are used interchangeably and refer to a peptide or polypeptide covalently attached to an Fc domain.

As used herein, the terms "protein" and "polypeptide" are used interchangeably and mean any chain of at least five naturally or non-naturally occurring amino acids linked by peptide bonds.

As used herein, the term "peptibody" refers to a polypeptide comprising one or more bioactive peptides joined together, optionally via linkers, with an Fc domain. See U.S. Pat. Nos. 6,660,843, 7,138,370 and 7,511,012 for examples of peptibodies.

As used herein, the term "Fab' fragment" refers to a structure containing one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an $F(ab')_2$ molecule.

As used herein, the term "$F(ab')_2$ fragment" refers to a structure containing two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains.

As used herein, the term "Fv region" refers to a structure comprising the variable regions from both the heavy and light chains, but lacks the constant regions.

As used herein, the term "domain antibody" refers to an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody can target the same or different antigens.

As used herein, the term "hemibody" refers to an immunologically functional immunoglobulin construct comprising a complete heavy chain, a complete light chain and a second heavy chain Fc region paired with the Fc region of the complete heavy chain. A linker can, but need not, be employed to join the heavy chain Fc region and the second heavy chain Fc region. In particular embodiments a hemibody is a monovalent form of an antigen binding protein disclosed herein. In other embodiments, pairs of charged residues can be employed to associate one Fc region with the second Fc region.

As used herein, the terms "bivalent antigen binding protein" or "bivalent antibody" refers to an antigen binding protein or antibody comprises two antigen binding sites. In some instances, the two binding sites have the same antigen specificities. Bivalent antigen binding proteins and bivalent antibodies can be bispecific, as described herein, and form aspects of the instant disclosure.

As used herein, the terms "multispecific antigen binding protein" or "multispecific antibody" when used in the context of a protein component is one that targets more than one antigen or epitope, and forms another aspect of the instant disclosure.

As used herein, the terms "bispecific," "dual-specific" or "bifunctional" when used in the context of an antigen binding protein or antibody protein component is a hybrid antigen binding protein or antibody, respectively, having two different antigen binding sites. Bispecific antigen binding proteins and antibodies are a species of multispecific antigen binding protein or multispecific antibody and can be produced by a variety of methods including, but not limited to, fusion of hybridomas or linking of Fab' fragments. See, e.g., Songsivilai and Lachmann, (1990) *Clin. Exp. Immunol.* 79:315-321; Kostelny et al., (1992) *J. Immunol.* 148:1547-1553. The two binding sites of a bispecific antigen binding protein or antibody will bind to two different epitopes, which can reside on the same or different protein targets.

As used herein, the term "Protein A" means any protein identical or substantially similar to Staphylococcal Protein A, including commercially available and/or recombinant forms of Protein A. For the purposes of this invention, Protein A specifically includes engineered Protein A derived media, such as Mab Select SuRe™ media (GE Healthcare), in which a single subunit (e.g., the B subunit) is replicated two or more times and joined in a contiguous sequence to form a recombinant Protein A molecule, and other non-naturally occurring Protein A molecules.

As used herein, the term "Protein G" means any protein identical or substantially similar to Streptococcal Protein G, including commercially available and/or recombinant forms of Protein G. Proteins A and G are often employed to purify antigen binding proteins (e.g., antibodies, peptibodies and other fusion proteins comprising a Fc region) by affinity chromatography. See, e.g., Vola et al. (1994), *Cell Biophys.* 24-25: 27-36; Aybay and Imir (2000), *J. Immunol. Methods* 233(1-2): 77-81; Ford et al. (2001), *J. Chromatogr. B* 754: 427-435. Proteins A and G are useful in this regard because they bind to the Fc region of these types of proteins. Recombinant fusion proteins comprising an Fc region of an IgG antibody can be purified using similar methods. Proteins A and G can be employed in the disclosed methods as an adsorbent component of a separation matrix.

As used herein, the terms "isolate" and "purify" are used interchangeably and mean to reduce by 1%, 2%, 3%, 4%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% and 99% or more, the amount of heterogenous elements, for example biological macromolecules such as proteins or DNA, that may be present in a sample comprising a protein of interest. The presence of heterogenous proteins can be assayed by any appropriate method including High-performance Liquid Chromatography (HPLC), gel electrophoresis and staining and/or ELISA assay. The presence of DNA and other nucleic acids can be assayed by any appropriate method including gel electrophoresis and staining and/or assays employing polymerase chain reaction.

As used herein, the term "protectant" and "additive" are used interchangeably and mean a compound having the ability to limit or modulate the extent of protein modification in response to UV-C dose level. A non-limiting list of protectants suitable for use in the disclosed methods includes one or more of tyrosine, tryptophan, methionine, pyridoxine and riboflavin. The term "protectant" encompasses single compounds as well as combinations of compounds, such as tyrosine and tryptophan, which can be present in any ratio relative to each other. As described herein, tyrosine has the lowest contribution to the overall UV absorbance.

As used herein, the term "dose of UV light" means an amount of energy delivered to a target in the form of UV light. The dose of UV light delivered to a target is a function of intensity and exposure time. A non-limiting list of examples of a "dose of UV light" includes about 1 $mJ/cm^2$, about 10 $mJ/cm^2$, about 25 $mJ/cm^2$, about 50 $mJ/cm^2$, about 75 $mJ/cm^2$, about 100 $mJ/cm^2$, about 125 $mJ/cm^2$, about 200 $mJ/cm^2$, about 250 $mJ/cm^2$, about 300 $mJ/cm^2$, about 350 $mJ/cm^2$, about 400 $mJ/cm^2$, about 450 $mJ/cm^2$, about 500 $mJ/cm^2$, about 600 $mJ/cm^2$, about 700 $mJ/cm^2$, about 800 $mJ/cm^2$, about 900 $mJ/cm^2$, about 1000 $mJ/cm^2$ and greater than about 1000 $mJ/cm^2$.

As used herein, the term "UV light" means the region of the light spectrum having a wavelength between at least 10 nm and at most 400 nm. By way of example, the term "UV light" encompasses light having a wavelength in the range of about 200 nm to about 280 nm, including a wavelength of about 254 nm. In the methods provided herein, UV light can be delivered in a uniform columnated and filtered fashion; accordingly, both uniform columnated and non columnated UV are encompassed by the term "UV light," as well as filtered UV light and unfiltered UV light.

As used herein, the term "sample comprising a protein component" means an aliquot of liquid comprising at least an aqueous component and a protein component. In various embodiments the aqueous component can comprise a buffer. The protein component can comprise any species comprising two or more amino acids joined by a peptide bond. A protein component can comprise all some or none of the 20 naturally-occurring amino acids, and the balance of the protein component can comprise any non-naturally occurring amino acid. Thus the methods provided herein can be performed on a sample comprising protein comprising one or more naturally-occurring amino acids or one or more non-naturally occurring amino acids. In various embodiments, a protein in a sample comprising a protein component is an antigen binding protein comprising one or more of a monoclonal antibody, a human antibody, a humanized antibody, a chimeric antibody, a recombinant antibody, a single chain antibody, a diabody, a triabody, a tetrabody, a Fab fragment, a $F(ab')_2$ fragment, an IgD antibody, an IgE antibody, an IgM antibody, an IgG1 antibody, an IgG2 antibody, an IgG3 antibody, or an IgG4 antibody, and fragments thereof, an Fc domain; a peptide; an Fc fusion protein; and a therapeutic protein.

As used herein, the term "reactive species" means any solution component that can or may react with another component to cause modification or oxidation the reacting component. A non-limiting list of examples of "reactive species" includes oxygen ions (e.g., $O^{2-}$), hydroxyl ions (e.g., $OH^-$) and peroxides (e.g., $H_2O_2$).

As used herein, the term "Water Factor" is a value calculated by the following equation:

$$\text{Water Factor} = \frac{1 - 10^{-al}}{al\ \ln(10)},$$

where a=absorbance of the solution and l is the pathlength in meters.

II. Method of Inactivating a Virus in a Sample

Viral inactivation is a critical step in the preparation of protein solutions for therapeutic use. Indeed, various regulatory agencies have established standards for virus inactivation and numerous vendors have attacked this problem. Viral inactivation technologies have developed in a number of directions, including filter technology, HTST and UV-C technology. While each of these technologies has its strength, each also has its drawbacks as well. In the case of UV-C, it has been observed that while it is an effective and efficient approach to inactivating viruses, extended exposure of proteins to UV-C light can lead to protein degradation and/or oxidation. Thus, while UV-C technology is an effective approach to inactivating viruses, the exposure of a sample comprising a protein to high doses of UV-C light can have adverse effects on the protein itself. Accordingly, in one aspect of the instant disclosure a method is provided in which the high doses of UV-C required to inactivate a virus in a sample comprising a protein component can be employed, while at the same time reducing or eliminating the potential for damage to the protein itself. Accordingly a method of inactivating a virus in a sample comprising a protein component is provided. In one embodiment the method can be performed as follows.

Initially, a sample comprising a protein component, wherein the sample is known or suspected to contain a virus is provided. The sample comprising a protein component can be of any composition, with the caveat that the sample contains a protein. For example, the sample can comprise eluant from a chromatography column that has been collected into a pool. In this embodiment the chromatography column pool can be collected from any type of chromatography operation. Examples of chromatography column pools include Protein A column eluant pool comprising the protein component, a Protein G column eluant pool comprising the protein component, a HIC column pool comprising the protein component, a SEC column pool comprising the protein component, an IEC column pool comprising the protein component, and a hydroxyapatite column pool comprising the protein component.

The sample comprising a protein component can also comprise a chromatography column eluant stream. For example, the eluant stream can be acquired as it exits a chromatography column; accordingly, the method can be performed in situ and in real time. Examples of chromatography eluant streams include a Protein A column effluent stream comprising the protein component, a Protein G column effluent stream comprising the protein component, a HIC column effluent stream comprising the protein component, a SEC column effluent stream comprising the protein component, an IEC column effluent stream comprising the protein component, and a hydroxyapatite column effluent stream comprising the protein component.

Although the disclosed method can be applied to a sample comprising any type of protein component, the disclosed method can be particularly beneficial in the context of a protein-based therapeutic, which is an area in which viral inactivation standards have been adopted. Thus, in one example a sample comprising a protein component is a sample comprising a protein-based pharmaceutical molecule. In particular embodiments the protein component of a sample of the disclosed method comprises an antigen binding protein (e.g., one or more of (i) an antigen binding protein comprising one or more of a monoclonal antibody, a human antibody, a humanized antibody, a chimeric antibody, a recombinant antibody, a single chain antibody, a diabody, a triabody, a tetrabody, a Fab fragment, a $F(ab')_2$ fragment, an IgD antibody, an IgE antibody, an IgM antibody, an IgG1 antibody, an IgG2 antibody, an IgG3 antibody, or an IgG4 antibody, and fragments thereof, (ii) an Fc domain; (iii) a peptide; (iv) an Fc fusion protein; and (v) a therapeutic protein), an Fc domain, a peptide and a therapeutic protein. These types of molecules are commonly identified as modalities for therapeutic molecules. With regard to antibody antigen binding proteins, as noted herein the term "antibody" implies fully human antibodies, humanized antibodies or fully non-human (e.g., murine) antibodies, and the disclosed method can be applied to all of these types of molecules.

In various embodiments of the disclosed method, a sample treated by the disclosed methods can be a sample comprising cells in which it is desired to inactivate a virus. Examples of such samples include a sample comprising platelet cells, CHO cells or bacterial cells, such as *E. coli*, in which it is desired to inactivate viruses. Such sample can comprise cell cultures. In these embodiments the method can be performed as described, with the substitution of a sample comprising cells for a sample comprising a protein component.

UV-C viral inactivation is most commonly applied to samples comprising a protein component, or to a sample comprising cells such as platelets, although this is not a requirement and in other embodiments the disclosed methods can also be employed to remove virus from a sample that does not comprise a protein component.

In one aspect, the disclosed methods are directed to the inactivation of viruses that can be unintentionally introduced into samples comprising a protein component. Possible sources of unintentional virus introduction in a protein production process include contaminated raw materials or exposure by manufacturing personnel. One advantage of the disclosed methods is that they can be employed on any type of virus, and is independent of whether the virus is enveloped or unenveloped. Thus, the method can be applied to double stranded DNA viruses, single stranded DNA viruses, double stranded RNA viruses and single stranded RNA viruses. Examples of virus families, which implicitly include all members of the family, that can be inactivated using the disclosed methods include adenoviridae, asfarviridae, herpesviridae, iridoviridae, papillomaviridae, polyomaviridae, poxviridae, circoviridae, hepadnaviridae, parvoviridae, birnaviridae, reoviridae, arenaviridae, vornaviridae, bunyaviridae, deltaviridae, filoviridae, orthomyxoviridae, paramyxoviridae, rhabdoviridae, arterioviridae, astroviridae, caliciviridae, cornonavirdae, flaviviridae, HEV-like viruses, nodaviridae, picornaviridae, togaviridae, and tertroviridae.

In particular embodiments, which can be particularly relevant to therapeutic protein production processes, viruses that can be inactivated using the disclosed methods include the parvovirus MVM, the retrovirus MuLV or the bunya virus CVV.

Continuing with the method, a target dose of UV light under which the virus is inactivated is identified. In order to most effectively and efficiently inactivate a virus using UV-C it is desirable to identify a target dose of UV-C that will achieve the desired result. Although the disclosed methods can be performed without optimizing UV-C exposure conditions (which collectively comprise a "UV-C dose") to the type of virus to be inactivated and the method performed at any convenient UV-C dose, the efficiency of the method can be enhanced by identifying a target dose specific to the virus to be inactivated. It is noted that some viruses can share conditions under which they will be inactivated by UV-C light, and by selecting appropriate exposure conditions two or more types of viruses can be inactivated in a single operation of the disclosed method. Various studies have been performed to identify the UV sensitivities of various DNA- and RNA-containing viruses. See, e.g., Lytle & Sagripanti, (2005) *J Virol.* 79:14244-252, and Knipe et al., (2007) *Field's Virology*, Lippincott Williams & Wilkins, which are incorporated herein by reference, and FIGS. 11 and 12.

Continuing, a protectant is then added to the sample to form a stabilized mixture. One function of the protectant is to scavenge reactive species that can degrade or modify components of the sample, e.g., protein in the sample, so as to reduce or eliminate any modification or degradation that may occur as a result of exposure of the sample to UV-C light. More particularly, exposure of a solution to the doses of UV-C light that are required for a particular operation, e.g., virus inactivation, can give rise to reactive species. In some cases, the presence of these reactive species in the sample may lead to undesired modifications, for example via indirect oxidation of sample components, including proteins. In other cases, the presence of reactive species in a sample may also contribute to the indirect modification of sample components. As noted herein, the possibility of protein modification and/or degradation is one of the challenges associated with the use of UV-C light in viral inactivation methods.

Examples of reactive species that can degrade or modify proteins include reactive species, such as oxygen ions (e.g., $O^{2-}$), hydroxyl ions (e.g., $OH^-$) and peroxides (e.g., $H_2O_2$). Since these and other reactive species are commonly generated during the exposure of a solution to UV-C light in the high doses often required for effective virus inactivation, it is preferable to add the protectant prior to exposure of the sample to UV light.

Not all chemical species can serve as a protectant. Indeed, as outlined in the Examples presented herein, a detailed search was performed to identify suitable protectants. A suitable protectant is a compound that has the ability to scavenge any reactive species present in the sample, such as those generated during a UV-C exposure, so that the effect of these reactive species on the components of the sample (e.g., protein) is reduced relative to the effect of the reactive species on the sample components in the absence of a protectant. In some cases degradation or modification of sample components due to exposure to reactive species generated during a UV-C operation can be eliminated entirely using a protectant.

In addition to its effectiveness in neutralizing undesired consequences of any reactive species present in a sample, another consideration when selecting a protectant is the difficulty associated with removing it from the sample following the UV-C exposure. When the disclosed method is applied to a sample comprising a therapeutic molecule such as an antigen binding protein (e.g., one or more of (i) an antigen binding protein comprising one or more of a monoclonal antibody, a human antibody, a humanized antibody, a chimeric antibody, a recombinant antibody, a single chain antibody, a diabody, a triabody, a tetrabody, a Fab fragment, a $F(ab')_2$ fragment, an IgD antibody, an IgE antibody, an IgM antibody, an IgG1 antibody, an IgG2 antibody, an IgG3 antibody, or an IgG4 antibody, and fragments thereof, (ii) an Fc domain; (iii) a peptide; (iv) an Fc fusion protein; and (v) a therapeutic protein) or therapeutic protein, this consideration becomes a very significant factor. Due to regulatory restraints on product quality, a desirable property of a protectant is the ability to remove it from a sample after it has performed its protective function.

Taking into account all the above properties of a desirable protectant, a list of suitable protectants is provided and includes, but is not limited to, tyrosine, tryptophan, methionine, pyridoxine and riboflavin. In various embodiments a protectant comprises two or more compounds in various proportions. For example, a protectant can comprise tyrosine, tryptophan or both tyrosine and tryptophan in any desired proportion. The precise composition and proportion of a combination of protectants can be determined empirically and/or as described herein.

Additional protectants can be readily identified using the instant disclosure as a guide. In one such screen a candidate protectant can be added to a sample comprising a protein, exposed to UV-C light in a dose suitable to inactivate one or more viruses (FIGS. 11 and 12, as well as the references provided herein can be used as a guide in establishing a relevant UV-C dose), and then examined to determine the extent of degradation or modification of the protein. Standard chromatographic and analytical techniques can be employed in this regard. For example, IEC can be employed to assess modification of a protein and SEC or mass spectrometry can be used to examine protein degradation.

A protectant employed in the disclosed methods can be added in any concentration. In a preferred embodiment the protectant is added to a concentration that will effectively reduce or eliminate modification or degradation of a component of a sample. The amount of protectant can be determined in an analogous fashion to the identification of a protectant. That is, a selected protectant can be added to a sample at an initial concentration, the sample exposed to UV-C light and the degree of degradation and/or modification of the sample component (e.g., protein) determined using established methodology. As in the case of the identification of a protectant, suitable techniques include IEC, SEC and mass spectrometry. If the protein component is not protected to the desired degree the assessment can be repeated until a concentration is identified that provides the required degree of protection. In one particular embodiment the protectant is added to the sample in a concentration ratio of greater than 1 part protectant to 200 parts protein. Stated another way, the protectant can be added to the sample in a concentration ratio of greater than 1 mM protectant to 200 mM protein (i.e., 1:200). Other concentration ratios that can be employed include 1:180, 1:170, 1:160, 1:150, 1:140, 1:130, 1:120, 1:110, 1:100, 1:90, 1:80, 1:70, 1:60, 1:50, 1:40, 1:30, 1:20 or 1:10.

Although the provided protectants and protectant concentrations can be employed as described, the identification of additional protectants and protectant concentrations can be readily performed using an empirical matrix-type approach. In one example of such an approach a matrix can be constructed with one axis embodying various candidate protectants and another axis embodying various concentration levels. Experiments can be performed as described (e.g., using SEC, IEC and/or mass spectrometry to assess the effect of a given protectant and concentration) to fill in the matrix with preferred protectants and preferred concentrations for those protectants. This approach will provide yet additional protectants and protectant concentrations.

Having formed a stabilized mixture comprising a sample comprising a protein component and a protectant the stabilized mixture is then exposed to UV light provided by a source operating at a selected power level and selected wavelength for a selected period of time. The combination of these parameters is collectively referred to herein as a UV-C dose. Examples of sources that can be employed in the disclosed method include the Newport Oriel® Flood UV-C sources, for example Model 97536.

A UV-C source is preferably adapted to be attuned to a range of power levels. Preferred power levels range from about 1 mJ to about 1000 mJ. In specific examples, the UV-C source is able to deliver about 1 mJ, about 10 mJ, about 25 mJ, about 50 mJ, about 75 mJ, about 100 mJ, about 125 mJ, about 200 mJ, about 250 mJ, about 300 mJ, about 350 mJ, about 400 mJ, about 500 mJ, about 600 mJ, about 700 mJ, about 800 mJ, about 900 mJ or about 1000 mJ. Another feature that is desirable for a UV-C source is the ability to switch from a first power level to a second power level either automatically in response to feedback from a monitor or manually by an operator.

A UV-C source is also preferably adapted to deliver UV-C light over a range of wavelengths. Preferred wavelengths range from about 200 nm to about 280 nm, which corresponds to the full C band of the UV spectrum. In particularly preferred embodiments the wavelength is about 254 nm.

When the protectant or combination of protectants is added to the sample to form the stabilized mixture the absorbance of the stabilized mixture may be different from the absorbance of a sample with no protectant added. For example, an added protectant(s) or other compounds present in the stabilized sample (e.g., buffer components, solubilization agents, etc) may absorb some of the UV light to which the sample is exposed. This can lead to a decrease in the effective UV light transmitted to any virus present in the sample and consequently a decrease in viral inactivation.

In order to account for the inherent absorbance of a protectant(s) and/or other solution components and ensure that the target dose of UV-C light is received by the stabilized mixture a feedback loop can be employed, wherein properties of the UV light exposure are varied in response to an assessment of UV mixture absorbance. Thus, following assessment of the mixture absorbance entering the UVC exposure device the properties of the exposure within the device (e.g., lamp power, residence time, or other means) can be transiently changed to ensure that stabilized mixture emerging from the device received the target dose. Such an assessment can alternatively be made by measurement of the absorbance of the mixture leaving the device or be made by measurement of mixture within the device. In one embodiment, such an assessment can be made by monitoring the absorbance of the sample at a specified wavelength, such as 254 nm. The absorbance data can be used to determine the dose received, and can be defined as an adjustment of delivered energy dose that takes into account the absorbance of ultraviolet light by components that may be contained in the sample (e.g., protein, protectant chemistries, or other solution chemicals). In one embodiment the assessment can be made by measuring the light source power at the solution surface. Alternatively the light source power can be measured at the lamp surface. Further, the electrical power drawn by the lamp can be measured to assess the light source power.

It is expected that the assessment will indicate a decrease in received dose due to the absorbance of the protectant(s) in the stabilized sample. Accordingly, one or more of the wavelength, the UV light source power and the UV light exposure time is then modulated if the assessment indicates the target dose of UV light has not been delivered to the stabilized mixture.

In one embodiment, for a well mixed vessel receiving a collimated beam of UVc radiation the dose can be adjusted by employing the formula:

$$\text{Water Factor} = \frac{1 - 10^{-al}}{al\ \ln(10)},$$

where a=absorbance of the solution and l is the pathlength. See, e.g., Bolton, (2003) *ASCE,* 129(3): 209-215. Having determined the Water Factor for a given virus inactivation operation, the target dose of UV light is divided by the Water Factor to determine the exposure time for treatment. In another embodiment, for a unmixed vessel receiving UVc radiation (e.g., thin-film process reactor or equivalent) the dose can be adjusted by employing the formula: dose~$(P/Q)\exp(-al)=(P_0/Q_0)\exp(-a_0l)$, where a=absorbance of the solution, and l is the pathlength of the annulas. In the formula, P is the power output of the lamp and Q is the volumetric flow rate for the mixture with absorbance=a; $P_0$ and $Q_0$ are the power and flowrate for a reference mixture with an absorbance=$a_0$. See, e.g., Ye, Z (2007) "UV Disinfection Between Concentric Cylinders" PhD dissertation, Georgia Institute of Technology It is noted that any or all steps of the disclosed methods can be carried out manually or by any convenient automated means, such as by employing automated or computer-controlled systems. In some embodiments the entire method can be automated. In other embodiments one or more steps can be automated. For example, the assessment of delivered dose and modulation in response to variations from target dose levels can form a single automated step. In one embodiment the stabilized sample is exposed to UV light and is simultaneously monitored for variations from the target dose. If variations from target are detected a control module can modulate the exposure time, exposure wavelength or power of the UV source so that the target dose is achieved. This can be done in real time in a feedback loop-type arrangement.

The disclosed method can be performed at any scale and either as a discrete unit operation or as a continuous connected process. In one embodiment of a discrete unit operation a stabilized sample of any volume is formed in a vessel. The vessel is then exposed to UV light (e.g., UV-C light) and subsequently an assessment of virus inactivation is performed. The operation can be repeated until any virus present in the sample is inactivated. Alternatively the assessment can be made continuously with the exposure to UV light. Following inactivation of the virus the sample can be transferred to a separate vessel for further processing or packaging.

In an embodiment of a continuous connected process, the stabilized sample can be formed from effluent from a previous purification step, with the protectant added to the effluent stream as it comes off a prior column. The protectant can be mixed with the effluent stream by virtue of any shear forces associated with the introduction of the protectant into the effluent stream. The stabilized sample can then pass through a device configured for continuous exposure of UV light to a sample passing through it. Once the target dose of UV light is achieved the stream can then be passed to a second purification operation, such as a purification step to remove undesired protectant(s) or other compounds present in the stabilized sample.

Figure 13:
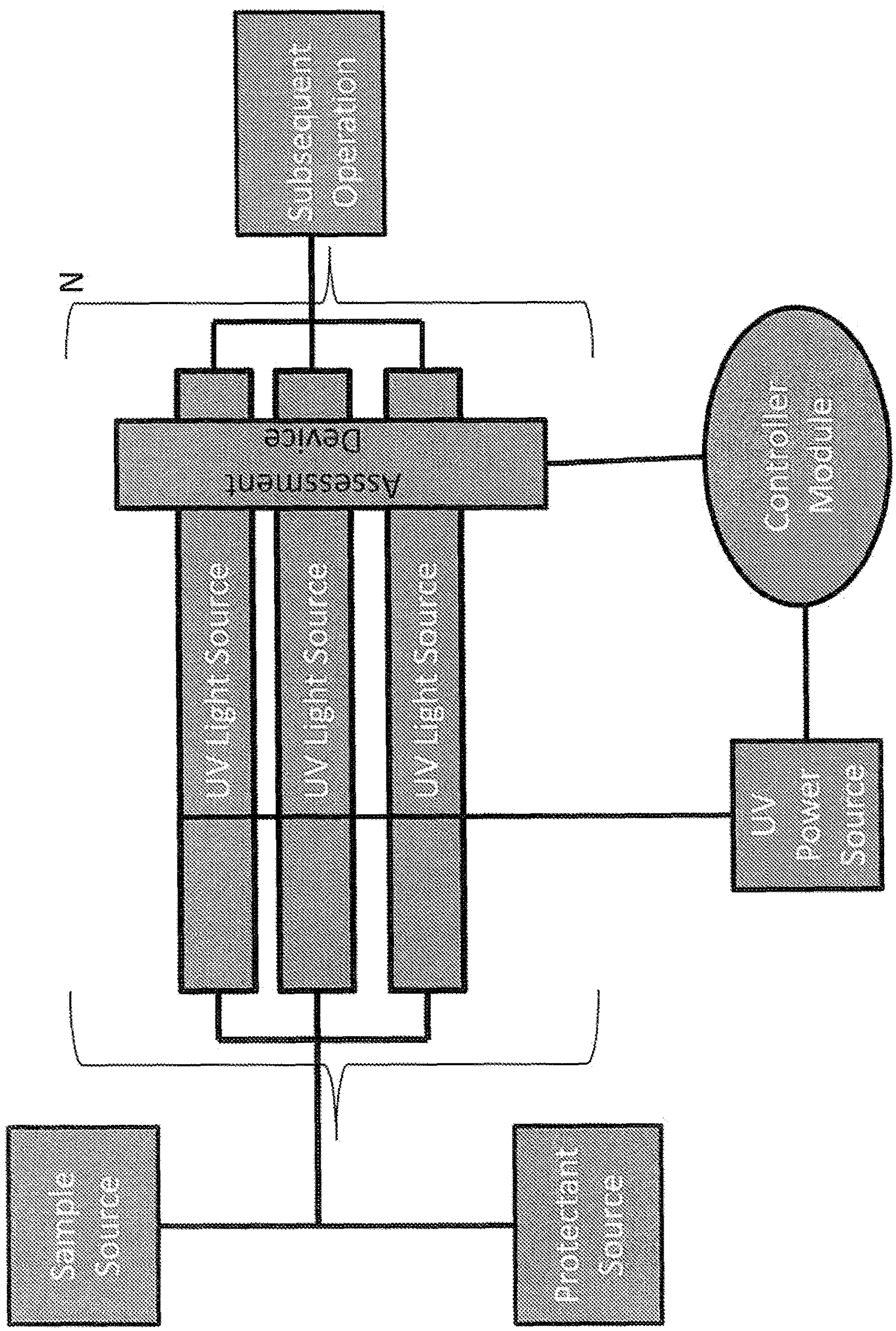
FIG. 13 is a schematic showing multiple UV-C sources running in parallel to accommodate large volumes of stabilized sample.
Figure 14:
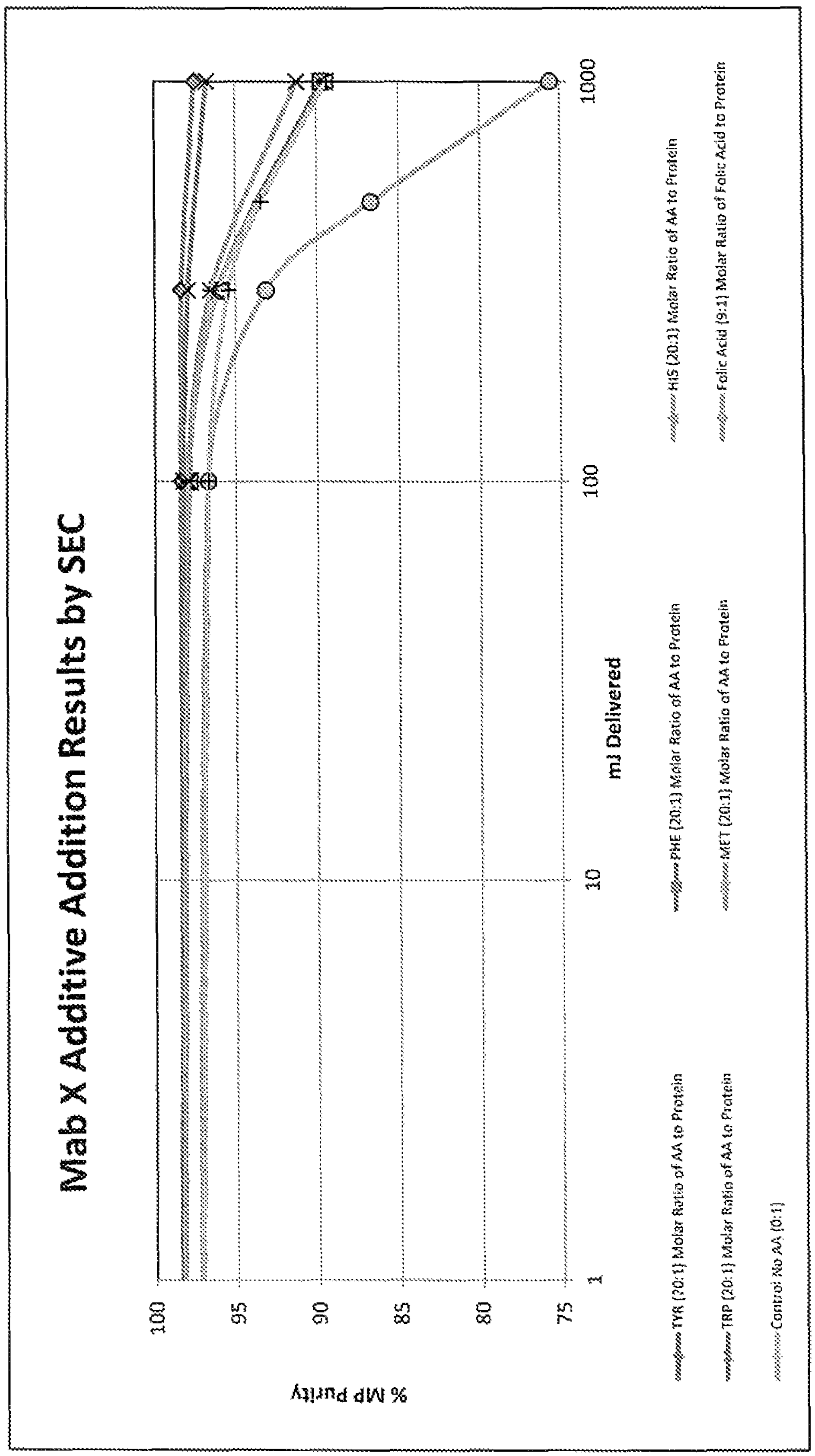
FIG. 14 is a plot of the main peak purity of a monoclonal antibody (Mab X) as a function of UV-C exposure in the presence a various protectants including tyrosine (TYR), tryptophan (TRP), phenylalanine (PHE), folic acid, methionine (MET) and histidine (HIS) as monitored by SEC-HPLC assay; the y-axis is plotted as % main peak, as a distribution of measured species and the x-axis is plotted as calculated dose delivered to the solution surface. The molar ratio of amino acid to Mab X is 20:1. A control of Mab X is also provided.
Figure 15:
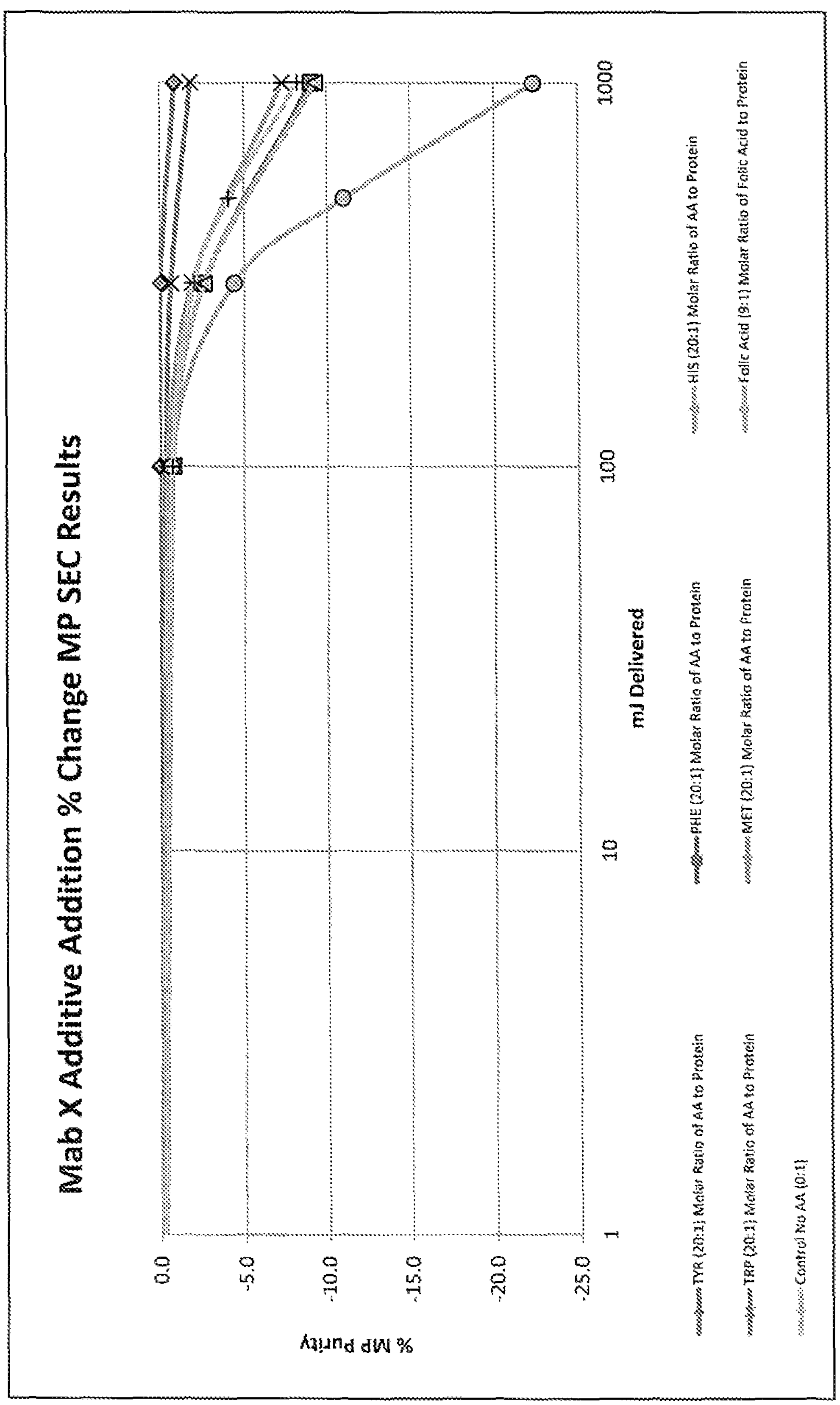
FIG. 15 is a plot of the main peak purity of a monoclonal antibody (Mab X) as a function of UV-C exposure in the presence a various protectants including tyrosine (TYR), tryptophan (TRP), phenylalanine (PHE), folic acid, methionine (MET) and histidine (HIS) as monitored by SEC-HPLC assay, and is presented as percent change from initial purity; the y-axis is plotted as normalized % change in main peak purity and the x-axis is plotted as calculated dose delivered to the solution surface. The molar ratio of amino acid to Mab X is 20:1. A control of Mab X is also provided.

In another aspect, the disclosed method can be performed on any scale, from bench scale to commercial scale. When performing the method on a commercial scale it may be convenient to split a stabilized sample into aliquots and treat each aliquot in parallel. For example, multiple UV-C sources can be run in parallel to accommodate large volumes of stabilized sample. FIG. 13 shows a schematic example of such a configuration.

III. Method of Reducing Protein Degradation or Modification Arising from the Presence of a Reactive Species Generated During Uv Exposure As described herein and shown in FIGS. 1-8, a sample comprising a protein component can undergo degradation or modification when exposed to UV light, particularly light in the UV-C band. The UV-C band, however, is the most effective region of the spectrum for a variety of purposes, e.g., inactivating viruses, and is of particular use in manufacturing applications. The observed protein degradation and/or modification can arise from the presence of reactive species, which are generated by the irradiation of the solvent component of a sample with UV light or ionizing radiation. Examples of reactive species include oxygen ions (e.g., $O^{2-}$), hydroxyl ions (e.g., $OH^-$) and peroxide species (e.g., $H_2O_2$). The presence of reactive species can have a deleterious effect on proteins. See, e.g., Cabiscol, et al., (2010) *Int. Microbiol,* 3:315 and Bandyopadhyay et al. (1999) *Curr. Sci.* 77:658-666.

In a protein production operation, the use of UV light can be employed to inactivate viruses but it may also facilitate protein degradation and/or modification. Thus, in one aspect the instant disclosure provides a method of reducing protein degradation or modification arising from the presence of a reactive species generated during UV exposure. In one embodiment the disclosed method can be performed as follows.

Initially, a sample comprising a protein component known or suspected to be degraded or modified in the presence of a reactive species is provided. The sample comprising a protein component can be of any composition, with the caveat that the sample contains a protein. For example, the sample can comprise eluant from a chromatography column that has been collected into a pool. In this embodiment the chromatography column pool can be collected from any type of chromatography operation. Examples of chromatography column pools include Protein A column eluant pool comprising the protein component, a Protein G column eluant pool comprising the protein component, a HIC column pool comprising the protein component, a SEC column pool comprising the protein component, an IEC column pool comprising the protein component, and a hydroxyapatite column pool comprising the protein component.

The sample comprising a protein component can also comprise a chromatography column eluant stream. For example, the eluant stream can be acquired as it exits a chromatography column; accordingly, the method can be performed in situ and in real time. Examples of chromatography eluant streams include a Protein A column effluent stream comprising the protein component, a Protein G column effluent stream comprising the protein component, a HIC column effluent stream comprising the protein component, a SEC column effluent stream comprising the protein component, an IEC column effluent stream comprising the protein component, and a hydroxyapatite column effluent stream comprising the protein component.

Although the disclosed method can be applied to a sample comprising any type of protein component, the disclosed method can be particularly beneficial in the context of a protein-based therapeutic, which is an area in which protein degradation and/or modification can be of significant concern. Thus, in one example a sample comprising a protein component is a sample comprising a protein-based pharmaceutical molecule. In particular embodiments the protein component of a sample of the disclosed method comprises an antigen binding protein (e.g., one or more of (i) an antigen binding protein comprising one or more of a monoclonal antibody, a human antibody, a humanized antibody, a chimeric antibody, a recombinant antibody, a single chain antibody, a diabody, a triabody, a tetrabody, a Fab fragment, a $F(ab')_2$ fragment, an IgD antibody, an IgE antibody, an IgM antibody, an IgG1 antibody, an IgG2 antibody, an IgG3 antibody, or an IgG4 antibody, and fragments thereof, (ii) an Fc domain; (iii) a peptide; (iv) an Fc fusion protein; and (v) a therapeutic protein), an Fc domain, a peptide and a therapeutic protein. These types of molecules are commonly identified as modalities for therapeutic molecules. With regard to antibodies, as noted herein the term "antibody" implies fully human antibodies, humanized antibodies or fully non-human (e.g., murine) antibodies, and the disclosed method can be applied to all of these types of molecules.

In various embodiments of the disclosed method, a sample treated by the disclosed methods can be a sample comprising cells in which it is desired to inactivate a virus. Examples of such samples include a sample comprising platelet cells, CHO cells or bacterial cells, such as *E. coli*, in which it is desired to inactivate viruses. Such sample can comprise cell cultures. In these embodiments the method can be performed as described, with the substitution of a sample comprising cells for a sample comprising a protein component.

Continuing with the method, a target dose of UV light is identified. The target dose can be selected for any reason but, in one preferred embodiment, a dose under which a virus of concern is inactivated is selected as the target dose. Using the selection of a target dose corresponding to a UV dose known or suspected to inactivate a particular virus of concern as an example, in order to most effectively and efficiently inactivate a virus using UV-C it is desirable to identify a target dose of UV-C that will achieve the desired result. Although the disclosed methods can be performed without optimizing UV-C exposure conditions (which collectively comprise a "UV-C dose") to the type of virus to be inactivated and the method performed at any convenient UV-C dose, the efficiency of the method can be enhanced by identifying a target dose specific to the virus to be inactivated. It is noted that some viruses can share conditions under which they will be inactivated by UV-C light, and by selecting appropriate exposure conditions two or more types of viruses can be inactivated in a single operation of the disclosed method. Various studies have been performed to identify the UV sensitivities of various DNA- and RNA-containing viruses. See, e.g., Lytle & Sagripanti, (2005) *J*

*Virol.* 79:14244-252, and Knipe et al., (2007) *Field's Virology*, Lippincott Williams & Wilkins, which are incorporated herein by reference, and FIGS. 11 and 12.

Continuing with the method, a protectant is then added to the sample to form a stabilized mixture. One function of the protectant is to scavenge reactive species that can degrade or modify components of the sample, e.g., protein in the sample, so as to reduce or eliminate any modification or degradation that may occur as a result of exposure of the sample to UV-C light. More particularly, exposure of a solution to the doses of UV-C light that are required can give rise to reactive species as described herein. Indeed, this is one of the challenges associated with the use of UV-C light in viral inactivation methods. The presence of these reactive species in the sample can lead to indirect oxidation of sample components, including proteins. Further, the presence of reactive species can also contribute to the indirect modification of sample components Examples of reactive species that can degrade or modify proteins include reactive species, such as oxygen ions (e.g., $O^{2-}$), hydroxyl ions (e.g., $OH^-$) and peroxides (e.g., $H_2O_2$). Since these and other reactive species are commonly generated during the exposure of a solution to UV-C light in the high doses often required for effective virus inactivation, it is preferable to add the protectant prior to exposure of the sample to UV light.

Not all chemical species can serve as a protectant. Indeed, as outlined in the Examples presented herein, a detailed search was performed to identify suitable protectants. A suitable protectant is a compound that has the ability to scavenge any reactive species present in the sample, such as those generated during a UV-C exposure, so that the effect of these reactive species on the components of the sample (e.g., protein) is reduced relative to the effect of the reactive species on the sample components in the absence of a protectant. In some cases degradation or modification of sample components due to exposure to reactive species generated during a UV-C operation can be eliminated entirely using a protectant.

In addition to its effectiveness in neutralizing undesired consequences of any reactive species present in a sample, another consideration when selecting a protectant is the difficulty associated with removing it from the sample following the UV-C exposure. When the disclosed method is applied to a sample comprising a therapeutic molecule such as an antigen binding protein (e.g., one or more of (i) an antigen binding protein comprising one or more of a monoclonal antibody, a human antibody, a humanized antibody, a chimeric antibody, a recombinant antibody, a single chain antibody, a diabody, a triabody, a tetrabody, a Fab fragment, a $F(ab')_2$ fragment, an IgD antibody, an IgE antibody, an IgM antibody, an IgG1 antibody, an IgG2 antibody, an IgG3 antibody, or an IgG4 antibody, and fragments thereof, (ii) an Fc domain; (iii) a peptide; (iv) an Fc fusion protein; and (v) a therapeutic protein) or therapeutic protein, this consideration becomes a very significant factor. Due to regulatory restraints on product quality, a desirable property of a protectant is the ability to remove it from a sample after it has performed its protective function.

Taking into account all the above properties of a desirable protectant, a list of suitable protectants is provided and includes, but is not limited to, tyrosine, tryptophan, methionine, pyridoxine and riboflavin. In various embodiments a protectant comprises two or more compounds in various proportions. For example, a protectant can comprise tyrosine, tryptophan or both tyrosine and tryptophan in any desired proportion. The precise composition and proportion of a combination of protectants can be determined empirically and/or as described herein.

Additional protectants can be readily identified using the instant disclosure as a guide. In one such screen a candidate protectant can be added to a sample comprising a protein, exposed to UV-C light in a dose suitable to inactivate one or more viruses (FIGS. 11 and 12, as well as the references provided herein can be used as a guide in establishing a relevant UV-C dose), and then examined to determine the extent of degradation or modification of the protein. Standard chromatographic and analytical techniques can be employed in this regard. For example, IEC can be employed to assess modification of a protein and SEC or mass spectrometry can be used to examine protein degradation.

A protectant employed in the disclosed methods can be added in any concentration. In a preferred embodiment the protectant is added to a concentration that will effectively reduce or eliminate modification or degradation of a component of a sample. The amount of protectant can be determined in an analogous fashion to the identification of a protectant. That is, a selected protectant can be added to a sample at an initial concentration, the sample exposed to UV-C light and the degree of degradation and/or modification of the sample component (e.g., protein) determined using established methodology. As in the case of the identification of a protectant, suitable techniques include IEC, SEC and mass spectrometry. If the protein component is not protected to the desired degree the assessment can be repeated until a concentration is identified that provides the required degree of protection. In one particular embodiment the protectant is added to the sample in a concentration ratio of greater than 1 part protectant to 200 parts protein. Stated another way, the protectant can be added to the sample in a concentration ratio of greater than 1 mM protectant to 200 mM protein (i.e., 1:200). Other concentration ratios that can be employed include 1:180, 1:170, 1:160, 1:150, 1:140, 1:130, 1:120, 1:110, 1:100, 1:90, 1:80, 1:70, 1:60, 1:50, 1:40, 1:30, 1:20 or 1:10.

Although the provided protectants and protectant concentrations can be employed as described, the identification of additional protectants and protectant concentrations can be readily performed using an empirical matrix-type approach. In one example of such an approach a matrix can be constructed with one axis embodying various candidate protectants and another axis embodying various concentration levels. Experiments can be performed as described (e.g., using SEC, IEC and/or mass spectrometry to assess the effect of a given protectant and concentration) to fill in the matrix with preferred protectants and preferred concentrations for those protectants. This approach will provide yet additional protectants and protectant concentrations.

Having formed a stabilized mixture comprising a sample comprising a protein component and a protectant the stabilized mixture is then exposed to UV light provided by a source operating at a selected power level and selected wavelength for a selected period of time. The combination of these parameters is collectively referred to herein as a UV-C dose. Examples of sources that can be employed in the disclosed method include the Newport Oriel® Flood UV-C sources, for example Model 97536.

A UV-C source is preferably adapted to be attuned to a range of power levels. Preferred power levels range from about 1 mJ to about 1000 mJ. In specific examples, the UV-C source is able to deliver about 1 mJ, about 10 mJ, about 25 mJ, about 50 mJ, about 75 mJ, about 100 mJ, about 125 mJ, about 200 mJ, about 250 mJ, about 300 mJ, about 350 mJ, about 400 mJ, about 450 mJ, about 500 mJ, about 600 mJ, about 700 mJ, about 800 mJ, about 900 mJ, about 1000 mJ or more than 1000 mJ. Another feature that is desirable for a UV-C source is the ability to switch from a first power level to a second power level either automatically in response to feedback from a monitor or manually by an operator.

A UV-C source is also preferably adapted to deliver UV-C light over a range of wavelengths. Preferred wavelengths range from about 200 nm to about 280 nm, which corresponds to the full C band of the UV spectrum. In particularly preferred embodiments the wavelength is about 254 nm.

When the protectant or combination of protectants is added to the sample to form the stabilized mixture the absorbance of the stabilized mixture may be different from the absorbance of a sample with no protectant added. For example, an added protectant(s) or other compounds present in the stabilized sample (e.g., buffer components, solubilization agents, etc) may absorb some of the UV light to which the sample is exposed. This can lead to a decrease in the effective UV light transmitted to any virus present in the sample and consequently a decrease in viral inactivation.

In order to account for the inherent absorbance of a protectant(s) and/or other solution components and ensure that the target dose of UV-C light is received by the stabilized mixture a feedback loop can be employed, wherein properties of the UV light exposure are varied in response to an assessment of UV mixture absorbance. Thus, following assessment of the mixture absorbance entering the UVC exposure device the properties of the exposure within the device (e.g., lamp power, residence time, or other means) can be transiently changed to ensure that stabilized mixture emerging from the device received the target dose. Such an assessment can alternatively be made by measurement of the absorbance of the mixture leaving the device or be made by measurement of mixture within the device. In one embodiment, such an assessment can be made by monitoring the absorbance of the sample at a specified wavelength, such as 254 nm. The absorbance data can be used to determine the dose received, and can be defined as an adjustment of delivered energy dose that takes into account the absorbance of ultraviolet light by components that may be contained in the sample (e.g., protein, protectant chemistries, or other solution chemicals). In one embodiment the assessment can be made by measuring the light source power at the solution surface. Alternatively the light source power can be measured at the lamp surface. Further, the electrical power drawn by the lamp can be measured to assess the light source power.

It is expected that the assessment will indicate a decrease in received dose due to the absorbance of the protectant(s) in the stabilized sample. Accordingly, one or more of the wavelength, the UV light source power and the UV light exposure time is then modulated if the assessment indicates the target dose of UV light has not been delivered to the stabilized mixture.

In one embodiment, for a well mixed vessel receiving a collimated beam of UVc radiation the dose can be adjusted by employing the formula:

$$\text{Water Factor} = \frac{1 - 10^{-al}}{al\ \ln(10)},$$

where a=absorbance of the solution and l is the pathlength. See, e.g., Bolton, (2003) *ASCE,* 129(3): 209-215. Having determined the Water Factor for a given virus inactivation operation, the target dose of UV light is divided by the Water Factor to determine the exposure time for treatment. In another embodiment, for a unmixed vessel receiving UVc radiation (e.g., thin-film process reactor or equivalent) the dose can be adjusted by employing the formula: dose~$(P/Q)\exp(-al)=(P_0/Q_0)\exp(-a_0 l)$, where a=absorbance of the solution, and l is the pathlength of the annulas. In the formula, P is the power output of the lamp and Q is the volumetric flow rate for the mixture with absorbance=a; $P_0$ and $Q_0$ are the power and flowrate for a reference mixture with an absorbance=$a_0$. See, e.g., Ye, Z (2007) "UV Disinfection Between Concentric Cylinders," PhD dissertation, Georgia Institute of Technology It is noted that any or all steps of the disclosed methods can be carried out manually or by any convenient automated means, such as by employing automated or computer-controlled systems. In some embodiments the entire method can be automated. In other embodiments one or more steps can be automated. For example, the assessment of delivered dose and modulation in response to variations from target dose levels can form a single automated step. In one embodiment the stabilized sample is exposed to UV light and is simultaneously monitored for variations from the target dose. If variations from target are detected a control module can modulate the exposure time, exposure wavelength or power of the UV source so that the target dose is achieved. This can be done in real time in a feedback loop-type arrangement.

The disclosed method can be performed at any scale and either as a discrete unit operation or as a continuous connected process. In one embodiment of a discrete unit operation a stabilized sample of any volume is formed in a vessel. The vessel is then exposed to UV light (e.g., UV-C light) and subsequently an assessment of virus inactivation is performed. The operation can be repeated until any virus present in the sample is inactivated. Alternatively the assessment can be made continuously with the exposure to UV light. Following inactivation of the virus the sample can be transferred to a separate vessel for further processing or packaging.

In an embodiment of a continuous connected process, the stabilized sample can be formed from effluent from a previous purification step, with the protectant added to the effluent stream as it comes off a prior column. The protectant can be mixed with the effluent stream by virtue of any shear forces associated with the introduction of the protectant into the effluent stream. The stabilized sample can then pass through a device configured for continuous exposure of UV light to a sample passing through it. Once the target dose of UV light is achieved the stream can then be passed to a second purification operation, such as a purification step to remove undesired protectant(s) or other compounds present in the stabilized sample.

In another aspect, the disclosed method can be performed on any scale, from bench scale to commercial scale. When performing the method on a commercial scale it may be convenient to split a stabilized sample into aliquots and treat each aliquot in parallel. For example, multiple UV-C sources can be run in parallel to accommodate large volumes of stabilized sample. FIG. 13 shows a schematic example of such a configuration.

IV. Method of Reducing Oxidation of Methionine Residues, Tryptophan Residues or Both Methionine and Tryptophan Residues in a Protein Subjected to UV Light In another aspect of the present disclosure a method of reducing oxidation of methionine residues, tryptophan residues or both methionine and tryptophan residues in a protein subjected to UV light is provided. As described herein and in the relevant literature, methionine and tryptophan residues are susceptible to oxidation, and can lead to protein inactivation. See, e.g., Schoneich, (2005) *Biochim Biophys Acta* 1703:111-19; Stadtman et al., (2003) *Antioxid. Redox. Signal* 5:577-82; Stadtman, (1993) *Ann. Rev. Biochem.* 62:797-821; and Dean et al., (1997) *Biochem. J.* 324:1-18. As noted throughout the instant disclosure, UV light is effective in various applications e.g., viral activation, which is its most common industrial application, but can lead to undesirable modifications and degradation of proteins. In some cases, modifications and/or degradations a protein may be directly or indirectly due to the presence of reactive species generated during UV exposure. On a molecular level, these reactive species can attack side chain residues in proteins, notably the side chains of methionine and tryptophan residues. In the context of a protein-based therapeutic these modifications can ultimately lead to the formation of high molecular weight species (e.g., aggregates and multimers) and low molecular weight species (e.g., fragmented proteins). The presence of these species in a therapeutic can translate into severe problems for patients taking the therapeutic.

In view of these potential problems it is desirable to eliminate the potential for modification and/or degradation of a protein, particularly a protein-based therapeutic. Accordingly, a method of reducing oxidation of methionine residues, tryptophan residues or both methionine and tryptophan residues in a protein subjected to UV light is provided. In one embodiment the disclosed method can be performed as follows.

Initially, a sample comprising a protein component comprising a methionine residue, a tryptophan residue or both a methionine and a tryptophan residue is provided. The sample comprising a protein component can be of any composition, with the caveat that the sample contains a protein and that the protein comprises a methionine residue, a tryptophan residue or both a methionine and a tryptophan residue. For example, the sample can comprise eluant from a chromatography column that has been collected into a pool. In this embodiment the chromatography column pool can be collected from any type of chromatography operation. Examples of chromatography column pools include Protein A column eluant pool comprising the protein component, a Protein G column eluant pool comprising the protein component, a HIC column pool comprising the protein component, a SEC column pool comprising the protein component, an IEC column pool comprising the protein component, and a hydroxyapatite column pool comprising the protein component.

The sample comprising a protein component can also comprise a chromatography column eluant stream. For example, the eluant stream can be acquired as it exits a chromatography column; accordingly, the method can be performed in situ and in real time. Examples of chromatography eluant streams include a Protein A column effluent stream comprising the protein component, a Protein G column effluent stream comprising the protein component, a HIC column effluent stream comprising the protein component, a SEC column effluent stream comprising the protein component, an IEC column effluent stream comprising the protein component, and a hydroxyapatite column effluent stream comprising the protein component.

Although the disclosed method can be applied to a sample comprising any type of protein component, the disclosed method can be particularly beneficial in the context of a protein-based therapeutic, which is an area in which protein modification and/or degradation via oxidation of methionine residue, a tryptophan residue or both a methionine and a tryptophan residue can render the protein-based therapeutic inactive or harmful to a patient. Thus, in one example a sample comprising a protein component is a sample comprising a protein-based pharmaceutical molecule. In particular embodiments the protein component of a sample of the disclosed method comprises an antigen binding protein (e.g., one or more of (i) an antigen binding protein comprising one or more of a monoclonal antibody, a human antibody, a humanized antibody, a chimeric antibody, a recombinant antibody, a single chain antibody, a diabody, a triabody, a tetrabody, a Fab fragment, a $F(ab')_2$ fragment, an IgD antibody, an IgE antibody, an IgM antibody, an IgG1 antibody, an IgG2 antibody, an IgG3 antibody, or an IgG4 antibody, and fragments thereof, (ii) an Fc domain; (iii) a peptide; (iv) an Fc fusion protein; and (v) a therapeutic protein), an Fc domain, a peptide and a therapeutic protein. These types of molecules are commonly identified as modalities for therapeutic molecules. With regard to antibodies, as noted herein the term "antibody" implies fully human antibodies, humanized antibodies or fully non-human (e.g., murine) antibodies, and the disclosed method can be applied to all of these types of molecules.

In various embodiments of the disclosed method, a sample treated by the disclosed methods can be a sample comprising cells in which it is desired to inactivate a virus. Examples of such samples include a sample comprising platelet cells, CHO cells or bacterial cells, such as *E. coli*. Such sample can comprise cell cultures. In these embodiments the method can be performed as described, with the substitution of a sample comprising cells for a sample comprising a protein component.

UV-C viral inactivation, which represents one application of the disclosed method, is most commonly applied to samples comprising a protein component, or to a sample comprising cells such as platelets, although this is not a requirement and in other embodiments the disclosed methods can also be employed to remove virus from a sample that does not comprise a protein component.

Continuing with the method, a target dose of UV light is identified. The target dose can be selected for any reason but, in one preferred embodiment, a dose under which a virus of concern is inactivated is selected as the target dose. Using the selection of a target dose corresponding to a UV dose known or suspected to inactivate a particular virus of concern as an example, in order to most effectively and efficiently inactivate a virus using UV-C it is desirable to identify a target dose of UV-C that will achieve the desired result. Although the disclosed methods can be performed without optimizing UV-C exposure conditions (which collectively comprise a "UV-C dose") to the type of virus to be inactivated and the method performed at any convenient UV-C dose, the efficiency of the method can be enhanced by identifying a target dose specific to the virus to be inactivated. It is noted that some viruses can share conditions under which they will be inactivated by UV-C light, and by selecting appropriate exposure conditions two or more types of viruses can be inactivated in a single operation of the disclosed method. Various studies have been performed to identify the UV sensitivities of various DNA- and RNA-containing viruses. See, e.g., Lytle & Sagripanti, (2005) *J Virol.* 79:14244-252, and Knipe et al., (2007) *Field's Virology*, Lippincott Williams & Wilkins, which are incorporated herein by reference, and FIGS. 11 and 12.

Continuing with the method, a protectant is then added to the sample to form a stabilized mixture. One function of the protectant is to scavenge reactive species that can degrade or modify components of the sample, e.g., protein in the sample, so as to reduce or eliminate any modification or degradation that may occur as a result of exposure of the sample to UV-C light. More particularly, exposure of a solution to the doses of UV-C light that are required can give rise to reactive species as described herein. Indeed, this is one of the challenges associated with the use of UV-C light in viral inactivation methods. The presence of these reactive species in the sample can lead to indirect oxidation of sample components, including proteins. Further, the presence of reactive species can also contribute to the indirect modification of sample components Examples of reactive species that can degrade or modify proteins include reactive species, such as oxygen ions (e.g., $O^{2-}$), hydroxyl ions (e.g., $OH^-$) and peroxides (e.g., $H_2O_2$). Since these and other reactive species are commonly generated during the exposure of a solution to UV-C light in the high doses often required for effective virus inactivation, it is preferable to add the protectant prior to exposure of the sample to UV light.

Not all chemical species can serve as a protectant. Indeed, as outlined in the Examples presented herein, a detailed search was performed to identify suitable protectants. A suitable protectant is a compound that has the ability to scavenge any reactive species present in the sample, such as those generated during a UV-C exposure, so that the effect of these reactive species on the components of the sample (e.g., protein) is reduced relative to the effect of the reactive species on the sample components in the absence of a protectant. In some cases degradation or modification of sample components due to exposure to reactive species generated during a UV-C operation can be eliminated entirely using a protectant.

In addition to its effectiveness in neutralizing undesired consequences of any reactive species present in a sample, another consideration when selecting a protectant is the difficulty associated with removing it from the sample following the UV-C exposure. When the disclosed method is applied to a sample comprising a therapeutic molecule such as an antigen binding protein (e.g., one or more of (i) an antigen binding protein comprising one or more of a monoclonal antibody, a human antibody, a humanized antibody, a chimeric antibody, a recombinant antibody, a single chain antibody, a diabody, a triabody, a tetrabody, a Fab fragment, a $F(ab')_2$ fragment, an IgD antibody, an IgE antibody, an IgM antibody, an IgG1 antibody, an IgG2 antibody, an IgG3 antibody, or an IgG4 antibody, and fragments thereof, (ii) an Fc domain; (iii) a peptide; (iv) an Fc fusion protein; and (v) a therapeutic protein) or therapeutic protein, this consideration becomes a very significant factor. Due to regulatory restraints on product quality, a desirable property of a protectant is the ability to remove it from a sample after it has performed its protective function.

Taking into account all the above properties of a desirable protectant, a list of suitable protectants is provided and includes, but is not limited to, tyrosine, tryptophan, methionine, pyridoxine and riboflavin. In various embodiments a protectant comprises two or more compounds in various proportions. For example, a protectant can comprise tyrosine, tryptophan or both tyrosine and tryptophan in any desired proportion. The precise composition and proportion of a combination of protectants can be determined empirically and/or as described herein.

Additional protectants can be readily identified using the instant disclosure as a guide. In one such screen a candidate protectant can be added to a sample comprising a protein, exposed to UV-C light in a dose suitable to inactivate one or more viruses (FIGS. 11 and 12, as well as the references provided herein can be used as a guide in establishing a relevant UV-C dose), and then examined to determine the extent of degradation or modification of the protein. Standard chromatographic and analytical techniques can be employed in this regard. For example, IEC can be employed to assess modification of a protein and SEC or mass spectrometry can be used to examine protein degradation.

A protectant employed in the disclosed methods can be added in any concentration. In a preferred embodiment the protectant is added to a concentration that will effectively reduce or eliminate modification or degradation of a component of a sample. The amount of protectant can be determined in an analogous fashion to the identification of a protectant. That is, a selected protectant can be added to a sample at an initial concentration, the sample exposed to UV-C light and the degree of degradation and/or modification of the sample component (e.g., protein) determined using established methodology. As in the case of the identification of a protectant, suitable techniques include IEC, SEC and mass spectrometry. If the protein component is not protected to the desired degree the assessment can be repeated until a concentration is identified that provides the required degree of protection. In one particular embodiment the protectant is added to the sample in a concentration ratio of greater than 1 part protectant to 200 parts protein. Stated another way, the protectant can be added to the sample in a concentration ratio of greater than 1 mM protectant to 200 mM protein (i.e., 1:200). Other concentration ratios that can be employed include 1:180, 1:170, 1:160, 1:150, 1:140, 1:130, 1:120, 1:110, 1:100, 1:90, 1:80, 1:70, 1:60, 1:50, 1:40, 1:30, 1:20 or 1:10.

Although the provided protectants and protectant concentrations can be employed as described, the identification of additional protectants and protectant concentrations can be readily performed using an empirical matrix-type approach. In one example of such an approach a matrix can be constructed with one axis embodying various candidate protectants and another axis embodying various concentration levels. Experiments can be performed as described (e.g., using SEC, IEC and/or mass spectrometry to assess the effect of a given protectant and concentration) to fill in the matrix with preferred protectants and preferred concentrations for those protectants. This approach will provide yet additional protectants and protectant concentrations.

Having formed a stabilized mixture comprising a sample comprising a protein component and a protectant the stabilized mixture is then exposed to UV light provided by a source operating at a selected power level and selected wavelength for a selected period of time. The combination of these parameters is collectively referred to herein as a UV-C dose. Examples of sources that can be employed in the disclosed method include the Newport Oriel® Flood UV-C sources, for example Model 97536.

A UV-C source is preferably adapted to be attuned to a range of power levels. Preferred power levels range from about 1 mJ to about 1000 mJ. In specific examples, the UV-C source is able to deliver about 1 mJ, about 10 mJ, about 25 mJ, about 50 mJ, about 75 mJ, about 100 mJ, about 125 mJ, about 200 mJ, about 250 mJ, about 300 mJ, about 350 mJ, about 400 mJ, about 450 mJ, about 500 mJ, about 600 mJ, about 700 mJ, about 800 mJ, about 900 mJ, about 1000 mJ or more than 1000 mJ. Another feature that is desirable for a UV-C source is the ability to switch from a first power level to a second power level either automatically in response to feedback from a monitor or manually by an operator.

A UV-C source is also preferably adapted to deliver UV-C light over a range of wavelengths. Preferred wavelengths range from about 200 nm to about 280 nm, which corresponds to the full C band of the UV spectrum. In particularly preferred embodiments the wavelength is about 254 nm.

When the protectant or combination of protectants is added to the sample to form the stabilized mixture the absorbance of the stabilized mixture may be different from the absorbance of a sample with no protectant added. For example, an added protectant(s) or other compounds present in the stabilized sample (e.g., buffer components, solubilization agents, etc) may absorb some of the UV light to which the sample is exposed. This can lead to a decrease in the effective UV light transmitted to any virus present in the sample and consequently a decrease in viral inactivation.

In order to account for the inherent absorbance of a protectant(s) and/or other solution components and ensure that the target dose of UV-C light is received by the stabilized mixture a feedback loop can be employed, wherein properties of the UV light exposure are varied in response to an assessment of UV mixture absorbance. Thus, following assessment of the mixture absorbance entering the UVC exposure device the properties of the exposure within the device (e.g., lamp power, residence time, or other means) can be transiently changed to ensure that stabilized mixture emerging from the device received the target dose. Such an assessment can alternatively be made by measurement of the absorbance of the mixture leaving the device or be made by measurement of mixture within the device. In one embodiment, such an assessment can be made by monitoring the absorbance of the sample at a specified wavelength, such as 254 nm. The absorbance data can be used to determine the dose received, and can be defined as an adjustment of delivered energy dose that takes into account the absorbance of ultraviolet light by components that may be contained in the sample (e.g., protein, protectant chemistries, or other solution chemicals). In one embodiment the assessment can be made by measuring the light source power at the solution surface. Alternatively the light source power can be measured at the lamp surface. Further, the electrical power drawn by the lamp can be measured to assess the light source power.

It is expected that the assessment will indicate a decrease in received dose due to the absorbance of the protectant(s) in the stabilized sample. Accordingly, one or more of the wavelength, the UV light source power and the UV light exposure time is then modulated if the assessment indicates the target dose of UV light has not been delivered to the stabilized mixture.

In one embodiment, for a well mixed vessel receiving a collimated beam of UVc radiation the dose can be adjusted by employing the formula:

$$\text{Water Factor} = \frac{1-10^{-al}}{al\ \ln(10)},$$

where a=absorbance of the solution and l is the pathlength. See, e.g., Bolton (2003) *ASCE* 129(3):209-215. Having determined the Water Factor for a given virus inactivation operation, the target dose of UV light is divided by the Water Factor to determine the exposure time for treatment. In another embodiment, for a unmixed vessel receiving UVc radiation (e.g., thin-film process reactor or equivalent) the dose can be adjusted by employing the formula: dose~$(P/Q)\exp(-al)=(P_0/Q_0)\exp(-a_0 l)$, where a=absorbance of the solution, and l is the pathlength of the annulas. In the formula, P is the power output of the lamp and Q is the volumetric flow rate for the mixture with absorbance=a; $P_0$ and $Q_0$ are the power and flowrate for a reference mixture with an absorbance=$a_0$. Ye, Z (2007) "UV Disinfection Between Concentric Cylinders," PhD dissertation, Georgia Institute of Technology It is noted that any or all steps of the disclosed methods can be carried out manually or by any convenient automated means, such as by employing automated or computer-controlled systems. In some embodiments the entire method can be automated. In other embodiments one or more steps can be automated. For example, the assessment of delivered dose and modulation in response to variations from target dose levels can form a single automated step. In one embodiment the stabilized sample is exposed to UV light and is simultaneously monitored for variations from the target dose. If variations from target are detected a control module can modulate the exposure time, exposure wavelength or power of the UV source so that the target dose is achieved. This can be done in real time in a feedback loop-type arrangement.

The disclosed method can be performed at any scale and either as a discrete unit operation or as a continuous connected process. In one embodiment of a discrete unit operation a stabilized sample of any volume is formed in a vessel. The vessel is then exposed to UV light (e.g., UV-C light) and subsequently an assessment of virus inactivation is performed. The operation can be repeated until any virus present in the sample is inactivated. Alternatively the assessment can be made continuously with the exposure to UV light. Following inactivation of the virus the sample can be transferred to a separate vessel for further processing or packaging.

In an embodiment of a continuous connected process, the stabilized sample can be formed from effluent from a previous purification step, with the protectant added to the effluent stream as it comes off a prior column. The protectant can be mixed with the effluent stream by virtue of any shear forces associated with the introduction of the protectant into the effluent stream. The stabilized sample can then pass through a device configured for continuous exposure of UV light to a sample passing through it. Once the target dose of UV light is achieved the stream can then be passed to a second purification operation, such as a purification step to remove undesired protectant(s) or other compounds present in the stabilized sample.

In another aspect, the disclosed method can be performed on any scale, from bench scale to commercial scale. When performing the method on a commercial scale it may be convenient to split a stabilized sample into aliquots and treat each aliquot in parallel. For example, multiple UV-C sources can be run in parallel to accommodate large volumes of stabilized sample. FIG. 13 shows a schematic example of such a configuration.

Various references have been provided in the instant disclosure. All references cited herein are incorporated in their entireties for any purpose.

EXAMPLES

The following examples demonstrate embodiments and aspects of the disclosed methods and are not intended to be limiting.

Example 1

Evaluation of Process Chemistry on Protein Modification Upon Exposure to UV-C Dose Three different recombinant proteins comprising an Fc moiety, namely IgG2 monoclonal antibodies, Mab X, Mab Y and Mab Z, were expressed in a mammalian expression system, namely CHO cells. The protein was separated from the cells and other solid debris by centrifugation and purified using Protein A chromatography resin. The protein was exchanged into solutions of different conditions, include salt ranges from 50-300 mM sodium acetate, pH ranges from 4.3 to 7.4, and protein concentrations of 2 to 30 g/L.

Following purification each of these protein aliquots was treated by exposure to UV-C light at a wavelength of 254 nM, delivered by a custom configured 500 watt Hg Newport Oreil® Flood exposure source (Model 97536). The exposure source was configured to provide uniform columnated and filtered light, over a range of 0 to 1000 mJ/cm$^2$ targeted dose received. Dose received was defined as an adjustment of delivered energy dose that takes into account the absorbance of ultraviolet light by components that may be contained in the sample (e.g., protein, protectant chemistries, or other solution chemicals). The dose was adjusted by the formula:

$$\text{Water Factor} = \frac{1-10^{-al}}{al\ \ln(10)},$$

where a=absorbance of the solution and l is the pathlength. The desired received dose was divided by the water factor to determine the target delivered dose setpoint for treatment. The dosing was achieved by measuring the light source power at the solution surface and adjusting the exposure time.

Each sample was analyzed for protein modification by one or all of: SEC-HPLC for aggregate level, CEX-HPLC for charge isoform levels, peptide map for amino acid residue modification, and cell-based bioactivity assay for potency comparison.

The observed results indicated that pH, conductivity, and protein concentration did not affect the level of protein modification significantly. These experiments confirmed that the main source of variation in protein purity and/or modification was the level of UV-C dose. FIGS. 1-8 summarize the effect of the UV-C exposure on the three monoclonal antibodies studied.

Example 2

Evaluation of Solution Additives on Protein Modification and Viral Inactivation Upon Exposure to UV-C Dose Having established that UV-C exposure, and not pH, conductivity or protein concentration, was responsible for the modification and/or degradation of the monoclonal antibody protein subjects, an intensive search was conducted to identify compounds that would protect the proteins from undesired effects associated with UV-C exposure.

A recombinant protein comprising an Fc moiety, monoclonal antibody Mab X, was expressed in a mammalian expression system, namely CHO cells. The protein was separated from the cells and other solid debris by centrifugation and purified using Protein A chromatography resin. The Protein A column elution pool was adjusted to pH 5.0 and either diluted or concentrated to concentrations of 2, 12, or 30 g/L protein concentration.

Following purification, a sample from each concentration was combined with an additive, at a ratio of 1 mM additive per 20 mM of protein. The additives included one or more of tyrosine, tryptophan, methionine, histidine, folic acid, phenylalanine, pyridoxine, and riboflavin. Each of these protein aliquots was treated by exposure to UV-C light at a wavelength of 254 nM, delivered by a custom configured Newport Oreil®Flood exposure source (Model 97536). The exposure source was configured to provide uniform columnated and filtered light, over a range of 0 to 1000 mJ/cm$^2$ targeted dose received. Dose received was defined as an adjustment of delivered energy dose that takes into account the absorbance of ultraviolet light by components that may be contained in the sample (e.g., protein, protectant chemistries, or other solution chemicals). This is adjusted by the formula:

$$\text{Water Factor} = \frac{1-10^{-al}}{al\ \ln(10)},$$

where a=absorbance of the solution and l is the pathlength. The desired received dose was divided by the water factor to determine the target delivered dose setpoint for treatment. The dosing was achieved by measuring the light source power at the solution surface and adjusting the exposure time.

Each sample was analyzed for protein modification by one or all of: SEC-HPLC for aggregate level, CEX-HPLC for charge isoform levels, peptide map for amino acid residue modification, and cell-based bioactivity assay for potency comparison. The results of these assays are shown in FIGS. 1-9.

The observed results indicated that some additives, namely Folic Acid and Histidine, did not affect the level of protein modification significantly, in a positive way, and that methionine showed a slight benefit. However, other additives, such as Tryptophan or Tyrosine had a significant positive effect in limiting the degree of protein modification relative to dose level of UV radiation, FIGS. 9-10 and 14-15 summarize the results of this investigation. It is surprising that tyrosine and tryptophan were effective protectants, while histidine and phenylalanine were significantly less protective or not protective. The ring structures found in tyrosine and tryptophan are similar to the structures found in phenylalanine and histidine. Tyrosine and phenylalanine are structurally very closely related amino acids. It was further surprising that methionine was not an effective protectant as it was noted to be significantly oxidized in protein treated with high doses of UV-C (FIGS. 7 and 8), whereas tryptophan was an effective protectant and was also noted to be oxidized in protein treated with high doses of UV-C.

Furthermore, it was demonstrated that the level of viral inactivation achieved (i.e., xmuLV) is responsive to UV-C dose level and can be practically significant (see FIG. 10), regardless of the presence of additives. The results of these experiments demonstrate that additives provide protection against UV-C mediated modification and do not adversely impact viral inactivation by UV dose level.

Example 3

Evaluation of In-Process Implementation of UV-C Treatment

Two different recombinant proteins comprising an Fc moiety, namely IgG2 monoclonal antibodies, Mab W and Mab X, were expressed in a mammalian expression system, namely CHO cells. The protein was separated from the cells and other solid debris by centrifugation and depth filtration.

Following purification, conditioning, and assessment, a series of pre-treatment samples were formed. Two sample legs were created: one derived from the centrifuged and depth-filtered material and another derived from further purification over a Protein chromatography resin and neutralization of that pool. Each of these pools were combined with a fluorescent coated microsphere tracer and then further divided into pools with and without addition of a protective additive, namely tyrosine. The individual stabilized mixtures were assessed for absorbance at 254 nm wavelength spectroscopy. Each of these stabilized protein mixtures were then treated by exposure to varying doses of UV-C light. Treatment was accomplished by passage of the mixture through an Atlantic UV Infinity® thin-film reactor containing a 33 watt Hq lamp. The mixture flowed through the 0.9 mm annular space formed between a quartz sleeve surrounding the 1.5 m lamp and a stainless steel shell.

Each pre-treatment pool was divided into separate dose exposure pools. The dose delivered within the reactor was adjusted by varying the exposure time via flow rate adjustment. The dose delivered was adjusted per the formula: dose~$(P/Q)\exp(-al)=(P_0/Q_0)\exp(-a_0l)$, where a=absorbance of the solution, and l is the pathlength of the annulas. In the formula, P is the power output of the lamp and Q is the volumetric flow rate for the mixture with absorbance=a; $P_0$ and $Q_0$ are the power and flowrate for a reference mixture with an absorbance=$a_0$.

Each sample was then analyzed for protein modification by SEC-HPLC for aggregate level (Table 1)

TABLE 1

Mab W with and without tyrosine protectant

| | Sample type | 254 nM Absorbance | Protectant | Flow rate | MD | 10% D | 90% D | % |
|---|---|---|---|---|---|---|---|---|
| 1 | DF | 24.8 | None | 1.16 | 8 | | | −0.2 |
| 2 | DF | 24.8 | None | 0.232 | 17 | | | −0.7 |
| 3 | DF | 24.8 | None | 0.116 | 30 | | | −1.8 |
| 4 | DF | 24.8 | None | 0.058 | 58 | | | −4.6 |
| 5 | DF | 24.8 | Tyr | 1.16 | 14 | | | −0.3 |
| 6 | DF | 24.8 | Tyr | 0.232 | 28 | | | −0.8 |
| 7 | DF | 24.8 | Tyr | 0.116 | 39 | | | −1.9 |
| 8 | DF | 24.8 | Tyr | 0.058 | 58 | | | −4.6 |
| 9 | PA | 10.4 | None | 2.60 | 19 | 7 | 42 | −1.1 |
| 10 | PA | 10.4 | None | 0.53 | 64 | 27 | 132 | −5.5 |
| 11 | PA | 10.4 | None | 0.26 | 83 | 31 | 172 | −7.9 |
| 12 | PA | 10.4 | None | 0.13 | 116 | 39 | 231 | −11.5 |
| 13 | PA | 10.4 | Tyr | 2.60 | 16 | 5 | 33 | −0.5 |
| 14 | PA | 10.4 | Tyr | 0.53 | 45 | 15 | 95 | −2.7 |
| 15 | PA | 10.4 | Tyr | 0.26 | 76 | 25 | 169 | −4.2 |
| 16 | PA | 10.4 | Tyr | 0.13 | 111 | 37 | 229 | −7.8 |

DF = Centrifuge and Depth Filter sample;
PA = Neutralized Protein-A Pool sample;
Tyr = tyrosine;
Flowrate is LPM,
MD = Mean Dose;
10% D = 10 Percentile Dose;
90% D = 90 Percentile Dose;
% = Change in % Main Peak SEC Purity

Example 4

Evaluation of In-Process and In-Line Implementation of UV-C Treatment

Three different recombinant proteins comprising an Fc moiety, namely monoclonal antibodies, are expressed in a mammalian expression system, namely CHO cells. The protein can be separated from the cells and other solid debris by centrifugation and purified using Protein A chromatography resin. The purified protein in the flowing Protein A effluent is passed through a surge-vessel, wherein it is conditioned with protectant to form the stabilized mixture, and subsequently assessed for absorbance at 254 nm wavelength by in-line absorption spectroscopy.

The flowing stabilized and assessed protein mixtures emerging from the surge vessel are treated by exposure to UV-C light. Treatment is accomplished by passage of the mixture through an Atlantic UV Infinity® thin-film reactor containing a 33 watt Hq lamp. The mixture flows through the 0.9 mm annular space formed between a quartz sleeve surrounding the 1.5 m lamp and a stainless steel shell.

The dose delivered within the reactor is adjusted by varying the lamp power or flow rate. The dose delivered is adjusted to account for the changing absorbance of the stabilized mixture emerging from the surge vessel so as to maintain a constant target received dose per the formula: dose~$(P/Q)\exp(-al)=(P_0/Q_0)\exp(-a_0l)$, where a=absorbance of the solution, and 1 is the pathlength of the annulas. In the formula, P is the power output of the lamp and Q is the volumetric flow rate for the mixture with absorbance=a; $P_0$ and $Q_0$ are the power and flowrate for a reference mixture with an absorbance=$a_0$.

Each sample is then analyzed for protein modification by one or all of: SEC-HPLC for aggregate level, CEX-HPLC for charge isoform levels, peptide map for amino acid residue modification, and cell-based bioactivity assay for potency comparison.

What is claimed is:

1. A method of inactivating a virus in a sample comprising an antibody comprising:

(a) providing a sample comprising the antibody, wherein the sample is known or suspected to contain a virus;

(b) adding a protectant to the sample to form a stabilized mixture, wherein the protectant comprises one or more of tyrosine, tryptophan, and methionine;

(c) measuring the absorbance of the stabilized mixture at 254 nm by in-line absorption spectroscopy;

(d) passing the stabilized mixture through a device configured to provide continuous exposure to UVC light such that a target dose of UVC light under which the virus is inactivated is delivered to the mixture;

(e) adjusting the UVC light exposure based on the absorbance measurement in (c) such that the target dose of UVC light is continually delivered to the stabilized mixture passing through the device, wherein steps (c), (d) and (e) are conducted as part of a real time automated feedback loop; and (f) removing the protectant from the mixture following exposure to UVC light.

2. The method of claim 1, wherein the sample comprises a chromatography column pool.

3. The method of claim 2, wherein the pool comprises one or more of a Protein A column eluant pool comprising the antibody, a Protein G column eluant pool comprising the antibody, a HIC column pool comprising the antibody, a SEC column pool comprising the antibody, an IEC column pool comprising the antibody, and a hydroxyapatite column pool comprising the antibody.

4. The method of claim 1, wherein the sample comprises a chromatography column effluent stream.

5. The method of claim 4, wherein the effluent stream comprises one or more of a Protein A column effluent stream comprising the antibody, a Protein G column effluent stream comprising the antibody, a HIC column effluent stream comprising the antibody, a SEC column effluent stream comprising the antibody, an IEC column effluent stream comprising the antibody, and a hydroxyapatite column effluent stream comprising the antibody.

6. The method of claim 1, wherein the antibody is a monoclonal antibody, a human antibody, a humanized antibody, a chimeric antibody, a recombinant antibody, a single chain antibody, an IgD antibody, an IgE antibody, an IgM antibody, an IgG1 antibody, an IgG2 antibody, an IgG3 antibody, or an IgG4 antibody.

7. The method of claim 1, wherein the virus comprises one or more of a dsDNA virus, a ssDNA virus, a dsRNA virus and a ssRNA virus.

8. The method of claim 7, wherein the virus comprises a virus of one or more of the virus families adenoviridae, asfarviridae, herpesviridae, iridoviridae, papillomaviridae, polyomaviridae, poxviridae, circoviridae, hepadnaviridae, parvoviridae, birnaviridae, reoviridae, arenaviridae, vornaviridae, bunyaviridae, deltaviridae, filoviridae, orthomyxoviridae, paramyxoviridae, rhabdoviridae, arterioviridae, astroviridae, caliciviridae, cornonavirdae, flaviviridae, REV-like viruses, nodaviridae, picornaviridae, togaviridae, and retroviridae.

9. The method of claim 8, wherein the virus is the parvovirus MVM, the retrovirus MuLV or the bunya virus CVV.

10. The method of claim 1, wherein the protectant is added to the sample in a concentration ratio of greater than 1 part protectant to 200 parts antibody.

11. The method of claim 1, wherein the protectant comprises (i) tyrosine; (ii) tryptophan; or (iii) tyrosine and tryptophan.

12. The method of claim 1, wherein the UVC light has a wavelength in the range of about 200 nm to about 280 nm.

13. The method of claim 12, wherein the UVC light has a wavelength of about 254 nm.

14. The method of claim 1, wherein the target dose is about 1 $mJ/cm^2$, about 10 $mJ/cm^2$, about 25 $mJ/cm^2$, about 50 $mJ/cm^2$, about 75 $mJ/cm^2$, about 100 $mJ/cm^2$, about 125 $mJ/cm^2$, about 200 $mJ/cm^2$, about 250 $mJ/cm^2$, about 300 $mJ/cm^2$, about 350 $mJ/cm^2$, about 400 $mJ/cm^2$, about 450 $mJ/cm^2$, about 500 $mJ/cm^2$, about 600 $mJ/cm^2$, about 700 $mJ/cm^2$, about 800 $mJ/cm^2$, about 900 $mJ/cm^2$, about 1000 $mJ/cm^2$ or greater than about 1000 $mJ/cm^2$.

15. The method of claim 1, wherein the method provides a viral log reduction value (LRV) of greater than or equal to about 0.5, about 1.0, about 1.5, about 2.0, about 2.5, about 3.0, about 3.5, about 4.0, about 4.5, about 5.0, about 5.5, about 6.0, about 6.5 or greater than about 6.5.

16. The method of claim 1, wherein the method is performed as a step in an antibody purification operation.

17. A method for inactivating a virus in a therapeutic antibody preparation comprising:

(a) providing a sample comprising the therapeutic antibody, wherein the sample is an effluent stream from an antibody purification step and the sample is known or suspected to contain a virus;

(b) introducing a protectant into the effluent stream to form a stabilized mixture, wherein the protectant comprises tyrosine, tryptophan, methionine, or combinations thereof, (c) measuring the absorbance of the stabilized mixture at 254 nm by in-line absorption spectroscopy;

(d) passing the stabilized mixture through a device configured to provide continuous exposure to UVC light such that a target dose of UVC light under which the virus is inactivated is delivered to the mixture;

(e) adjusting the flow rate of the stabilized mixture through the device or the lamp power of the device based on the absorbance measurement in (c) such that the target dose of UVC light is continually delivered to the stabilized mixture passing through the device, wherein steps (c), (d) and (e) are conducted as part of a real time automated feedback loop; and (f) removing the protectant from the mixture following UVC light exposure.

18. The method of claim 17, wherein the absorbance of the stabilized mixture is measured at 254 nm by in-line absorption spectroscopy.

19. The method of claim 17, wherein the sample is an effluent stream from a Protein A column.

20. The method of claim 17, wherein the sample is an effluent stream from a depth filtration step.

21. The method of claim 17, wherein the therapeutic antibody is a monoclonal antibody, a human antibody, a humanized antibody, a chimeric antibody, a recombinant antibody, a single chain antibody, an IgD antibody, an IgE antibody, an IgM antibody, an IgG1 antibody, an IgG2 antibody, an IgG3 antibody, or an IgG4 antibody.

22. The method of claim 17, wherein the target dose is about 1 $mJ/cm^2$, about 10 $mJ/cm^2$, about 25 $mJ/cm^2$, about 50 $mJ/cm^2$, about 75 $mJ/cm^2$, about 100 $mJ/cm^2$, about 125 $mJ/cm^2$, about 200 $mJ/cm^2$, about 250 $mJ/cm^2$, about 300 $mJ/cm^2$, about 350 $mJ/cm^2$, about 400 $mJ/cm^2$, about 450 $mJ/cm^2$, about 500 $mJ/cm^2$, about 600 $mJ/cm^2$, about 700 $mJ/cm^2$, about 800 $mJ/cm^2$, about 900 $mJ/cm^2$, about 1000 $mJ/cm^2$ or greater than about 1000 $mJ/cm^2$.

23. The method of claim 22, wherein the target dose is about 100 $mJ/cm^2$ or greater.

24. The method of claim 22, wherein the target dose is about 1000 $mJ/cm^2$ or greater.

25. The method of claim 17, wherein the method provides a viral LRV of greater than or equal to about 3.0, about 3.5, about 4.0, about 4.5, about 5.0, about 5.5, about 6.0, about 6.5 or greater than about 6.5.

26. The method of claim 17, wherein the UVC light has a wavelength in the range of about 200 nm to about 280 nm.

27. The method of claim 26, wherein the UVC light has a wavelength of about 254 nm.

28. The method of claim 17, wherein the virus comprises one or more of a dsDNA virus, a ssDNA virus, a dsRNA virus and a ssRNA virus.

29. The method of claim 28, wherein the virus comprises a virus of one or more of the virus families adenoviridae, asfarviridae, herpesviridae, iridoviridae, papillomaviridae, polyomaviridae, poxviridae, circoviridae, hepadnaviridae, parvoviridae, birnaviridae, reoviridae, arenaviridae, vornaviridae, bunyaviridae, deltaviridae, filoviridae, orthomyxoviridae, paramyxoviridae, rhabdoviridae, arterioviridae, astroviridae, caliciviridae, cornonavirdae, flaviviridae, HEV-like viruses, nodaviridae, picornaviridae, togaviridae, and retroviridae.

30. The method of claim 29, wherein the virus is the parvovirus MVM, the retrovirus MuLV or the bunya virus CVV.

31. The method of claim 1, wherein the dose of UVC light delivered to the stabilized mixture is adjusted by varying the flow rate of the stabilized mixture through the device.

32. The method of claim 1, wherein the dose of UVC light delivered to the stabilized mixture is adjusted by varying the lamp power of the device.

33. A method of inactivating a virus in a sample comprising an antibody, the method comprises the steps of:

(a) providing a sample comprising the antibody, wherein the sample is known or suspected to contain a virus;

(b) adding a protectant to the sample to form a stabilized mixture, wherein the protectant comprises one or more of tyrosine, tryptophan, and methionine;

(c) assessing the stabilized mixture for absorbance at 254 nm by in-line absorption spectroscopy;

(d) adjusting the lamp power or residence time within a device configured to provide continuous exposure to UV-light, based on the absorbance measurement in (c), such that a target dose of UVC light is delivered to the stabilized mixture as it passes through the device;

(e) passing the stabilized mixture through the device such that the target dose of UVC light is delivered to the mixture;

(f) conducting steps (c), (d), and (e) in that order as part of a real time automated feedback loop; and (g) removing the protectant from the mixture following exposure to UVC light.

34. The method according to claim 33, wherein the device is a quartz-containing device.

* * * * *